US011633256B2

(12) United States Patent
Izadyyazdanabadi et al.

(10) Patent No.: US 11,633,256 B2
(45) Date of Patent: Apr. 25, 2023

(54) SYSTEMS, METHODS, AND MEDIA FOR SELECTIVELY PRESENTING IMAGES CAPTURED BY CONFOCAL LASER ENDOMICROSCOPY

(71) Applicant: DIGNITY HEALTH, San Francisco, CA (US)

(72) Inventors: Mohammadhassan Izadyyazdanabadi, Tempe, AZ (US); Mark C. Preul, Scottsdale, AZ (US); Evgenii Belykh, Phoenix, AZ (US)

(73) Assignee: DIGNITY HEALTH, San Francisco, CA (US)

( * ) Notice: Subject to any disclaimer, the term of this patent is extended or adjusted under 35 U.S.C. 154(b) by 802 days.

(21) Appl. No.: 16/485,701

(22) PCT Filed: Feb. 14, 2018

(86) PCT No.: PCT/US2018/018240
§ 371 (c)(1),
(2) Date: Aug. 13, 2019

(87) PCT Pub. No.: WO2018/152248
PCT Pub. Date: Aug. 23, 2018

(65) Prior Publication Data
US 2020/0129263 A1 Apr. 30, 2020

Related U.S. Application Data

(60) Provisional application No. 62/458,886, filed on Feb. 14, 2017.

(51) Int. Cl.
A61B 5/00 (2006.01)
A61B 9/00 (2006.01)
(Continued)

(52) U.S. Cl.
CPC ............ A61B 90/37 (2016.02); A61B 5/0068 (2013.01); A61B 5/7267 (2013.01);
(Continued)

(58) Field of Classification Search
None
See application file for complete search history.

(56) References Cited

U.S. PATENT DOCUMENTS 9,275,308 B2 * 3/2016 Szegedy .............. G06V 10/454
2008/0058593 A1 3/2008 Gu
(Continued)

FOREIGN PATENT DOCUMENTS

WO 2008024419 A1 2/2008
WO 2013109624 A2 7/2013
(Continued)

OTHER PUBLICATIONS

Grisan et al., "Computer-Assisted Automated Image Recognition of Celiac Disease using Confocal Endomicroscopy," 2014 IEEE 11th International Symposium on Biomedical Imaging (ISBI), May 2014 (Year: 2014).*
(Continued)

Primary Examiner — Soo Shin
(74) Attorney, Agent, or Firm — Quarles & Brady LLP

(57) ABSTRACT

In accordance with some embodiments of the disclosed subject matter, systems, methods, and media for selectively presenting images captured by confocal laser endomicroscopy (CLE) are provided. In some embodiments, a method comprises: receiving images captured by a CLE device during brain surgery; providing the images to a convolution neural network (CNN) trained using at least a plurality of images of brain tissue captured by a CLE device and labeled diagnostic or non-diagnostic; receiving an indication, from the CNN, likelihoods that the images are diagnostic images;
(Continued)

determining, based on the likelihoods, which of the images are diagnostic images; and in response to determining that an image is a diagnostic image, causing the image to be presented during the brain surgery.

21 Claims, 12 Drawing Sheets

(51) Int. Cl.
- G06K 9/62 (2022.01)
- G06N 3/04 (2006.01)
- A61B 90/00 (2016.01)
- G16H 30/20 (2018.01)
- G06N 3/08 (2023.01)

(52) U.S. Cl.
CPC ......... *A61B 90/361* (2016.02); *G06N 3/0454* (2013.01); *G06N 3/08* (2013.01); *G16H 30/20* (2018.01); *A61B 2090/373* (2016.02)

(56) References Cited

U.S. PATENT DOCUMENTS

| | | |
|---|---|---|
| 2011/0280457 A1 | 11/2011 | Nielsen |
| 2014/0294266 A1 | 10/2014 | Eichhorn |
| 2015/0170002 A1 | 6/2015 | Szegedy et al. |
| 2016/0364522 A1 | 12/2016 | Frey et al. |
| 2018/0204046 A1* | 7/2018 | Bhattacharya ....... G06V 20/698 |
| 2020/0129263 A1* | 4/2020 | Izadyyazdanabadi ...................... G06N 3/0454 |

FOREIGN PATENT DOCUMENTS

| | | | |
|---|---|---|---|
| WO | 2014140841 A1 | 9/2014 | |
| WO | 2017023569 A1 | 2/2017 | |
| WO | WO-2017023569 A1 * | 2/2017 | ........... A61B 5/0042 |

OTHER PUBLICATIONS

Atreya et al., "In vivo imaging using fluorescent antibodies to tumor necrosis factor predicts therapeutic response in Crohn's disease," Nature Medicine, vol. 20, No. 3 Mar. 2014 (Year: 2014).*
Shin et al., "Deep Convolutional Neural Network for Computer-Aided Detection: CNN Architectures, Dataset Characteristics and Transfer Learning," IEEE Transactions on Medical Imaging, vol. 35, No. 5, May 2016 (Year: 2016).*
Rudy et al., "Neural Network Regularization via Robust Weight Factorization," arXiv:1412.6630 (Year: 2015).*
Abdi, A. H., et al. Automatic quality assessment of echocardiograms using convolutional neural networks: Feasibility on the apical four-chamber view, IEEE Transactions on Medical Imaging. Apr. 2017.
Belykh, E., et al. "Intraoperative fluorescence imaging for personalized brain tumor resection: current state and future directions." Frontiers in surgery 3 (2016): 55.
Bovik, A. C., "Automatic prediction of perceptual image and video quality," Proceedings of the IEEE 101(9), 2008-2024 (2013).
Charalampaki, P., et al., "Confocal laser endomicroscopy for real-time histomorphological diagnosis: Our clinical experience with 150 brain and spinal tumor cases," Neurosurgery 62, 171-176 (2015).
Christodoulidis, S., et al. "Multisource transfer learning with convolutional neural networks for lung pattern analysis." IEEE journal of biomedical and health informatics 21.1 (2016): 76-84.
Ciancio, A., et al., "No-reference blur assessment of digital pictures based on multifeature classifiers," IEEE Transactions on image processing 20(1), 64-75 (2011).
Ciresan, D. et al, Multi-column deep neural networks for image classification, in: Computer Vision and Pattern Recognition (CVPR), 2012 IEEE Conference on, IEEE, 2012, pp. 3642-3649.
Ciresan, D. et al., Deep neural networks segment neuronal membranes in electron microscopy images, in: Advances in neural information processing systems, 2012, pp. 2843-2851.
Corchs, S., et al., "No-reference image quality classification for jpeg-distorted images," Digital Signal Processing 30, 86-100 (2014).
Dietterich, T. G. et al., Ensemble methods in machine learning, Multiple classifier systems 1857 (2000) 1-15.
Erickson, B. J., "Irreversible compression of medical images," Journal of Digital Imaging 15(1), 5-14 (2002).
Fawcett, T., "Roc graphs: Notes and practical considerations for researchers," Machine learning 31(1), 1-38 (2004).
Foersch, S., et al., "Confocal laser endomicroscopy for diagnosis and histomorphologic imaging of brain tumors in vivo," PLoS One 7(7), e41760 (2012).
Gao, Y. et al, Describing ultrasound video content using deep convolutional neural networks, in: Biomedical Imaging (ISBI), 2016 IEEE 13th International Symposium on, IEEE, 2016, pp. 787-790.
Ghafoorian, M., et al., Deep multi-scale location-aware 3d convolutional neural networks for automated detection of lacunes of presumed vascular origin, NeuroImage: Clinical 14 (Feb. 4, 2017) 391-399.
Greenspan, H. et al, Guest editorial deep learning in medical imaging: Overview and future promise of an exciting new technique, IEEE Transactions on Medical Imaging 35 (5) (2016) 1153-1159.
Han, S., et al. "Deep compression: Compressing deep neural networks with pruning, trained quantization and huffman coding." arXiv preprint arXiv:1510.00149 Feb. 2016.
Hemami, S. S. et al, "No-reference image and video quality estimation: Applications and human-motivated design," Signal processing: Image communication 25(7), 469-481 (2010).
International Searching Authority, International Search Report and Written Opinion for application PCT/US2018/018240, dated Feb. 14, 2018. 18 pages.
Izadyyazdanabadi, M. et al, Improving utility of brain tumor confocal laser en-domicroscopy: objective value assessment and diagnostic frame detection with convolutional neural networks, in: SPIE Medical Imaging, International Society for Optics and Photonics, Mar. 2017, pp. 101342J-101342J.
Jia, Y., et al., "Caffe: Convolutional architecture for fast feature embedding," arXiv preprint arXiv:1408.5093 (2014).
Kamen, A., et al., "Automatic tissue differentiation based on confocal endomicroscopic images for intraoperative guidance in neurosurgery," BioMed research international 2016 (2016).
Karpathy. CS231n Convolutional Neural Networks for Visual Recognition. Jan. 2017. Retrieved from the Internet: URL https://web.archive.org/web/20170119170124/http://cs231n.github.io:80/.
Krizhevsky, A., et al., "ImageNet classification with deep convolutional neural networks," Advances in neural information processing systems, pp. 1097-1105 (2012).
Krogh, A. et al., Neural network ensembles, cross validation, and active learning, in: Advances in neural information processing systems, 1995, pp. 231-238.
Kumar, A. et al, An ensemble of fine-tuned convolutional neural networks for medical image classification, IEEE journal of biomedical and health informatics 21 (1) (Jan. 2017) 31-40.
Kumar, A. et al, Plane identification in fetal ultrasound images using saliency maps and convolutional neural networks, in: Biomedical Imaging (ISBI), 2016 IEEE 13th International Symposium on, IEEE, 2016, pp. 791-794.
Lecun, Y. et al., "The handbook of brain theory and neural networks," ch. Convolutional networks for images, speech, and time series, 255-258, MIT Press, Cambridge, MA, USA (1998).
Litjens, G. et al, A survey on deep learning in medical image analysis, arXiv preprint arXiv:1702.05747. Jun. 2017.
Mahapatra, D. et al. Retinal image quality classification using saliency maps and cnns, in: International Workshop on Machine Learning in Medical Imaging, Springer, 2016, pp. 172-179.
Martirosyan, N. L., et al., "Prospective evaluation of the utility of intraoperative confocal laser endomicroscopy in patients with brain neoplasms using fluorescein sodium: experience with 74 cases," Neurosurgical focus 40(3), E11 (2016).

(56) References Cited

OTHER PUBLICATIONS

Metz C.E., Basic principles of roc analysis, in: Seminars in nuclear medicine, vol. 8, Elsevier, 1978, pp. 283-298.

Mittal, A., et al., "No-reference approaches to image and video quality assessment," Multimedia Quality of Experience (QoE): Current Status and Future Requirements, 99 (2015).

Mollahosseini, A, et al. "Going Deeper in Facial Expression Recognition using Deep Neural Networks." arXiv preprint arXiv:1511.04110 (Nov. 2015).

Mooney, M. A. et al, Immediate ex-vivo diagnosis of pituitary adenomas using confocal reflectance microscopy: a proof-of-principle study, Journal of Neurosurgery. 2018.

Salehi, S.S.M. et al, Auto-context convolutional neural network (auto-net) for brain extraction in magnetic resonance imaging, IEEE Transactions on Medical Imaging. Jun. 2017.

Sanai, N., et al., "Intraoperative confocal microscopy for brain tumors: a feasibility analysis in humans," Neurosurgery 68, ons282-ons290 (2011).

Shi, J. et al., Multimodal neuroimaging feature learning with multimodal stacked deep polynomial networks for diagnosis of alzheimer's disease, IEEE journal of biomedical and health informatics. (Jan. 2017).

Sirinukunwattana, K. et al, Locality sensitive deep learning for detection and classification of nuclei in routine colon cancer histology images, IEEE transactions on medical imaging 35 (5) (2016) 1196-1206.

Srivastava, N. et al, Dropout: A simple way to prevent neural networks from overfitting, The Journal of Machine Learning Research 15 (1) (2014) 1929-1958.

Suk, H.I., Deep ensemble sparse regression network for alzheimers disease diagnosis, in: International Workshop on Machine Learning in Medical Imaging, Springer, 2016, pp. 113-121.

Szegedy, C., et al., "Going deeper with convolutions," Proceedings of the IEEE conference on Computer Vision and Pattern Recognition, pp. 1-9 (2015).

Szegedy, C., et al. "Inception-v4, inception-resnet and the impact of residual connections on learning." Thirty-first AAAI conference on artificial intelligence. Feb. 12, 2017.

Tajbakhsh, N. et al, Convolutional neural networks for medical image analysis: full training or fine tuning?, IEEE transactions on medical imaging 35 (5) (2016) 1299-1312.

Vosinski, J. et al, How transferable are features in deep neural networks?, in: Advances in neural information processing systems, 2014, pp. 3320-3328.

Zehri, AH et al, Neurosurgical confocal endomicroscopy: A review of contrast agents, confocal systems, and future imaging modalities, Surgical neurology international 5 (2014) 60.

Zhao, L. et al, Multiscale cnns for brain tumor segmentation and diagnosis, Computational and mathematical methods in medicine 2016.

Zhao, J. et al, Automatic detection and classification of leukocytes using convolutional neural networks, Medical & biological engineering & computing (2016) 1-15.

Zhou, Z.H. et al, Ensembling neural networks: many could be better than all, Artificial intelligence 137 (1-2) (2002) 239-263.

Shahid, M., et al. "No-reference image and video quality assessment: a classification and review of recent approaches." EURASIP Journal on image and Video Processing Jan. 2014. (2014): 40.

\* cited by examiner

SYSTEMS, METHODS, AND MEDIA FOR SELECTIVELY PRESENTING IMAGES CAPTURED BY CONFOCAL LASER ENDOMICROSCOPY

CROSS-REFERENCE TO RELATED APPLICATIONS

This application is the U.S. National Stage of PCT Application No. PCT/US2018/018240, filed Feb. 14, 2018, which is based on, and claims the benefit of U.S. Provisional Patent Application No. 62/458,886, filed Feb. 14, 2017, which is hereby incorporated herein by reference in its entirety for all purposes.

STATEMENT REGARDING FEDERALLY SPONSORED RESEARCH

N/A

BACKGROUND

Handheld Confocal Laser Endomicroscopy ("CLE") devices can be used during neurosurgery related to the treatment of brain tumors to aid neurosurgeons in distinguishing tissue that is part of a tumor from healthy tissue. These CLE devices can provide real-time (or near real-time) cellular-scale images of histopathological features of the tissue in vivo during surgery by capturing images at a rate of about one or more per second. Accordingly, over the course of use during a surgery or examination of tissue, a large number of total images are generated (e.g., on the order of hundreds to thousands). However, many of the images of brain tissue captured by CLE devices during brain surgery are not diagnostically useful. For example, while a wide range of fluorophores can be used for imaging using CLE devices in gastroenterology applications, fluorophore options that are available for in vivo use in the human brain may not be as effective as fluorophores that can be used in other applications.

More particularly, some of the images captured by CLE devices while using fluorescein sodium ("FNa") can include artifacts produced by motion of the probe, or by blood blocking at least a portion of the field of view of the CLE device. Images with such artifacts may not be useful in making a diagnostic determination. It may take significant amounts of time for the surgeon or pathologist to sort non-diagnostic frames (e.g., frames that do not include features that are useful for making a diagnostic determination, frames that include artifacts that render the frame unusable for diagnosis, etc.) from diagnostic frames (e.g., frames that include features that are useful for making a diagnostic determination, and that do not include artifacts that render the frame unusable for diagnosis, etc.) during the operation to make an intraoperative diagnosis. In some cases, if the surgeon wishes to make an intraoperative diagnosis using the images from the CLE device, the time it takes to sort through the images can increase the length of the surgery compared to an ideal case where the surgeon or pathologist making the diagnosis were presented with only diagnostically relevant images. For example, one study concluded that about half of the images acquired using a CLE device were non-diagnostic due to the abundance of motion and blood artifacts, or lack of histopathological features. FIG. 1 shows examples of non-diagnostic images captured using CLE techniques. FIG. 2 shows examples of diagnostic images captured using CLE techniques.

With the ongoing growth of medical imaging technologies, which are able to produce large numbers of images, assessment of image quality is becoming more important to take the burden off practitioners in selecting diagnostic images, and allowing the practitioners to focus on making diagnostic determinations. However, as described above, artifacts may be introduced to the images during the acquisition of the image, with some of the most common artifacts in images captured by CLE including blurring, noise and low/inhomogeneous contrast.

Artifacts can be included in CLE images for a variety of reasons. For example, blurring can occur in CLE images from a maladjusted focal plane (sometimes referred to as focal blur) or from relative motion between the probe and brain tissue under examination (sometimes referred to as motion blur). As another example, environmental noise can be introduced in the detectors. As yet another example, aliasing can cause a variety of artifacts including unwanted jagged edges, geometric distortions and inhomogeneity of contrast. While many non-useful images are distorted due to motion or blood artifacts, many other images without artifacts also lack diagnostic features immediately informative to the physician. Examining all the hundreds, or thousands, of images from a single case to discriminate diagnostic images from non-diagnostic images can be tedious and time consuming.

Existing techniques for objective quality assessment of medical images are often unable to accurately estimate diagnostic quality, and may inaccurately determine the visual quality of the image. For example, using a metric such as the entropy in the image to determine whether an image is likely to be diagnostic was not successful. In one approach that used entropy, the technique had very high sensitivity, but produced results with low accuracy and low specificity.

Accordingly, new systems, methods, and media for selectively presenting images captured by confocal laser endomicroscopy are desirable.

SUMMARY

In accordance with some embodiments of the disclosed subject matter, systems, methods, and media for selectively presenting images captured by confocal laser endomicroscopy are provided.

In accordance with some embodiments of the disclosed subject matter, a method for selectively presenting images captured by a confocal laser endomicroscopy (CLE) device is provided, the method comprising: receiving a first image captured by a first CLE device during brain surgery; providing the first image to a convolution neural network trained using at least a plurality of images, wherein each of the plurality of images is an image of brain tissue that was captured by a second CLE device and is labeled as either a diagnostic image or a non-diagnostic image; receiving an indication, based on a first output of the convolution neural network, of a first likelihood that the first image is a diagnostic image; determining, based on the first likelihood, that the first image is a diagnostic image; and in response to determining that the first image is a diagnostic image, causing the first image to be presented during the brain surgery.

In some embodiments, the method further comprises: receiving a second image captured by the first CLE device during the brain surgery; providing the second image to the convolution neural network; receiving an indication, based on a second output of the convolution neural network, of a second likelihood that the second image is a diagnostic image; determining, based on the second likelihood, that the second image is not a diagnostic image; in response to determining that the second image is not a diagnostic image, inhibiting the second image from being presented during the brain surgery.

In some embodiments, determining that the first image is a diagnostic image comprises determining that the first likelihood is at least a threshold probability.

In some embodiments, the threshold probability is about 0.5.

In some embodiments, the method further comprises: receiving a plurality of additional images captured by the CLE device during the brain surgery at a rate of between about 0.8 and about 1.2 frames per second; classifying each of the plurality of additional images in real time during the brain surgery using the convolution neural network; indicating, based on the classifications output by the convolutional neural network, that a first subset of the plurality of additional images are diagnostic images; and indicating, based on the classification output by the convolutional neural network, that a second subset of the plurality of plurality of additional images are non-diagnostic image.

In some embodiments, the method further comprises: receiving, by a server, the first image from a computing device that communicates with the CLE device over a local connection, and that is remote from the server; and sending, to the remote computing device, an indication that the first image is a diagnostic image.

In some embodiments, the method further comprises storing, by the server, the first image in memory associated with the server in connection with an indication that the first image is a diagnostic image.

In some embodiments, an architecture of the convolutional neural network is based on an AlexNet convolutional neural network.

In some embodiments, an architecture of the convolutional neural network is based on a GoogLeNet convolutional neural network.

In accordance with some embodiments of the disclosed subject matter, a system is provided, the system comprising: CLE device, comprising: a rigid probe, and a light source, wherein the confocal laser endomicroscopy device configured to generate image data representing brain tissue during brain surgery; and a computing device comprising: a hardware processor, and memory storing computer-executable instructions that, when executed by the processor, cause the processor to: receive, from the CLE device, a first image captured during a brain surgery; provide the first image to a convolution neural network trained using at least a plurality of images, wherein each of the plurality of images is an image of brain tissue that was captured using CLE techniques, and is labeled as either a diagnostic image or a non-diagnostic image; receive an indication, based on a first output of the convolution neural network, of a first likelihood that the first image is a diagnostic image; determine, based on the first likelihood, that the first image is a diagnostic image; and in response to determining that the first image is a diagnostic image, present the first image during the brain surgery.

In some embodiments, the computer-executable instructions, when executed by the processor, further cause the processor to: receive a second image captured by the CLE device during the brain surgery; provide the second image to the convolution neural network; receive an indication, based on a second output of the convolution neural network, of a second likelihood that the second image is a diagnostic image; determine, based on the second likelihood, that the second image is not a diagnostic image; in response to determining that the second image is not a diagnostic image, inhibit the second image from being presented during the brain surgery.

In some embodiments, the computer-executable instructions, when executed by the processor, further cause the processor to: receive, from the CLE device, a plurality of additional images captured by the CLE device during the brain surgery at a rate of between about 0.8 and about 1.2 frames per second; classify each of the plurality of additional images in real time during the brain surgery using the convolution neural network; indicate, based on the classifications output by the convolutional neural network, that a first subset of the plurality of additional images are diagnostic images; and indicating, based on the classification output by the convolutional neural network, that a second subset of the plurality of plurality of additional images are non-diagnostic image.

In some embodiments, the convolutional neural network is executed by the computing device.

In some embodiments, the convolutional neural network is executed by a remote server.

In accordance with some embodiments of the disclosed subject matter, a method for selectively presenting images captured by a CLE device is provided, the method comprising: receiving an image captured by a CLE device during brain surgery; providing the first image to a plurality of convolution neural networks trained using at least a subset of images from a plurality of images, wherein the plurality of images are images of brain tissue captured using CLE techniques and is labeled as either a diagnostic image or a non-diagnostic image, and wherein each of the plurality of convolutional neural networks was trained with a validation subset from the plurality of images that is different than the validation subset used to train each of the other convolution neural networks in the plurality of convolutional neural networks; receiving an indication, based on first outputs of the plurality of convolution neural networks, of a first likelihood that the first image is a diagnostic image; determining, based on the first likelihood, that the first image is a diagnostic image; and in response to determining that the first image is a diagnostic image, causing the first image to be presented during the brain surgery.

In some embodiments, the indication of the first likelihood is calculated based on a combination of the outputs of each of the plurality of convolutional neural networks.

In some embodiments, the first likelihood is the arithmetic mean of the outputs of each of the plurality of convolutional neural networks.

In some embodiments, the first likelihood is the geometric mean of the outputs of each of the plurality of convolutional neural networks.

In some embodiments, the method further comprises: receiving input, for each of the plurality of images, an indication of whether the image is diagnostic or non-diagnostic; dividing the plurality of images into a development subset and a testing subset; and dividing the development subset into l folds, wherein l is the number of convolutional neural networks in the plurality of convolutional neural networks; and training each of the l convolutional neural networks using l–1 of the folds as a training set and using one of the folds as a validation set, wherein each of the l convolutional neural networks is trained using a different fold as the validation set.

In some embodiments, a plurality of layers of each of the plurality of convolutional neural networks is trained using weights that are initialized to values set based on weights in a pre-trained convolutional neural network with the same architecture, wherein the pre-trained convolutional neural network was trained to recognize a multitude of classes of common objects.

In some embodiments, the multitude of classes of common objects correspond to at least a portion of the classes defined by the ImageNet dataset of labeled images.

DETAILED DESCRIPTION

Figure 1:
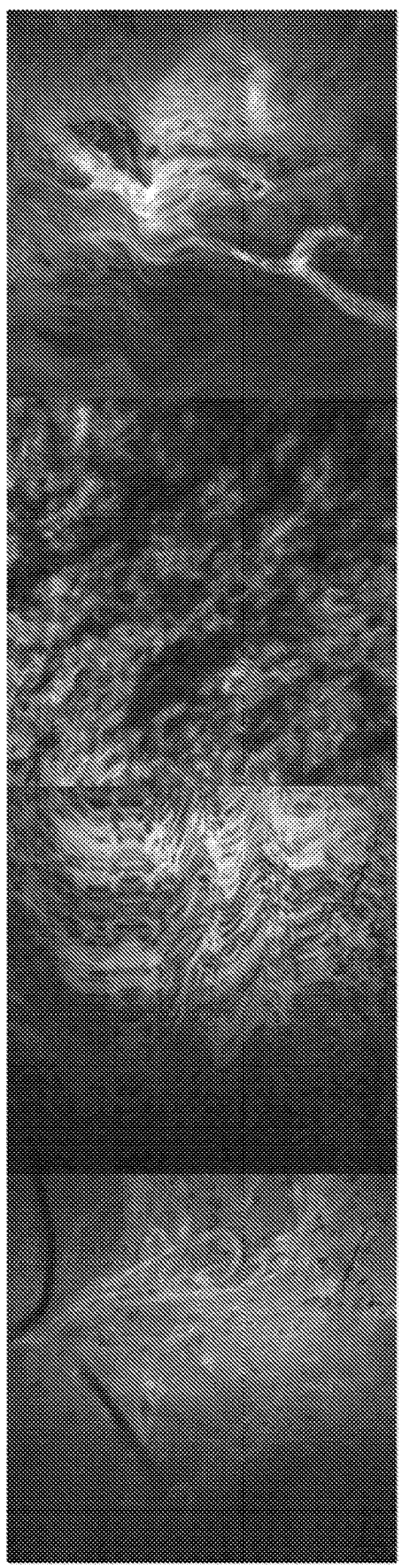
FIG. 1 shows examples of non-diagnostic images captured using CLE techniques.
Figure 1:
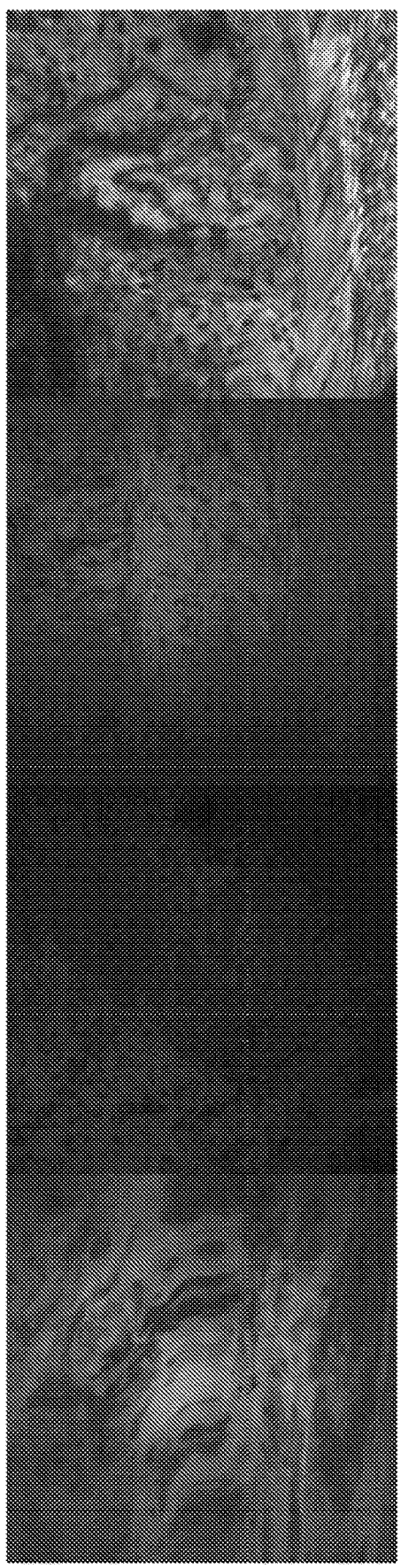
Figure 2:
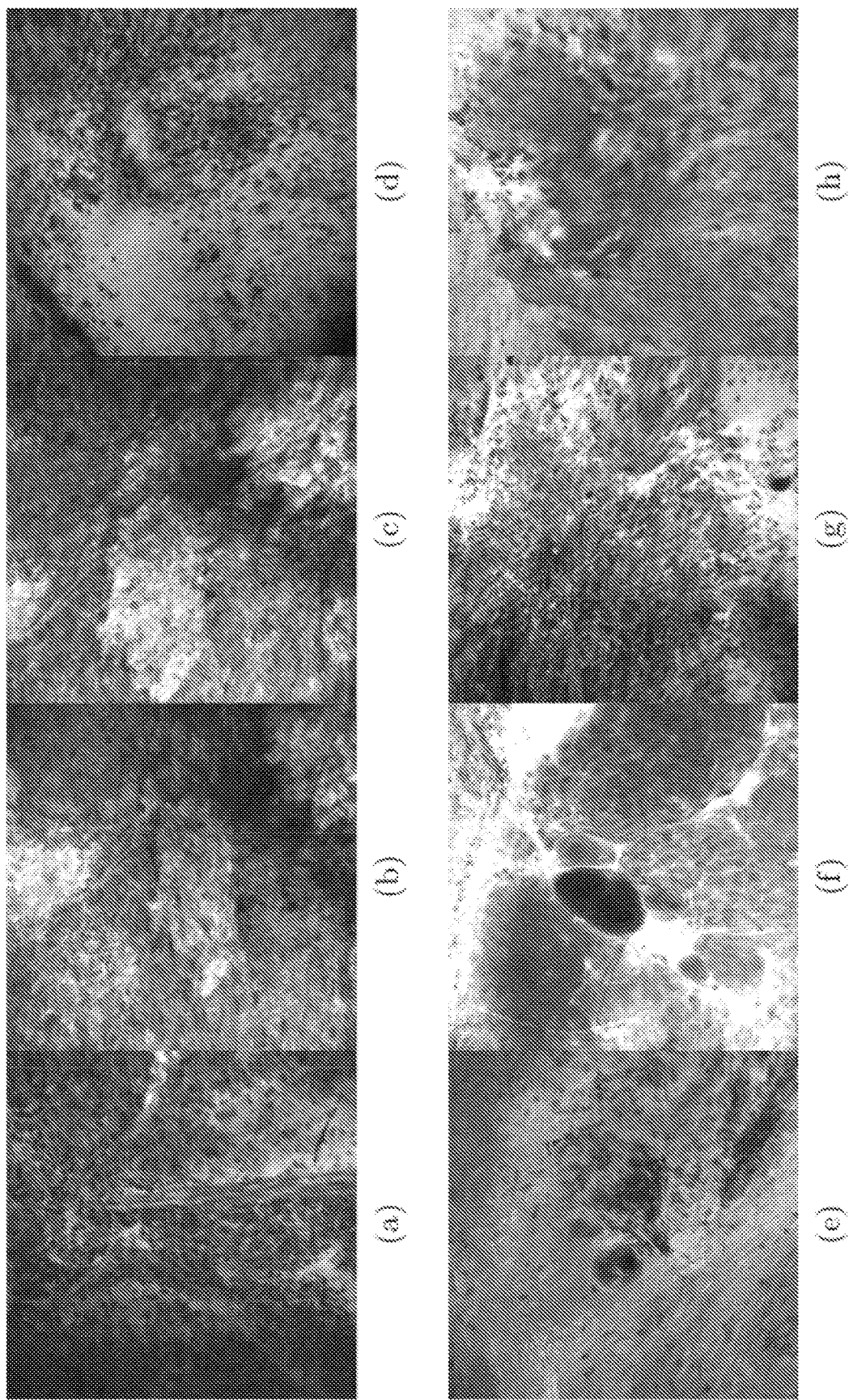
FIG. 2 shows examples of diagnostic images captured using CLE techniques.

In accordance with some embodiments of the disclosed subject matter, systems, methods, and media for selectively presenting images captured by confocal laser endomicroscopy are provided.

In general, image quality assessment ("IQA") techniques can be characterized as subjective assessment techniques, objective assessment techniques, or some combination thereof, which is sometimes referred to as hybrid image assessment. Any of these IQA techniques can be performed with some level of comparison to a reference image, or with no comparison to a reference image. For example, image assessments can be performed by comparison of the image being assessed with an original image used as a reference, which is sometimes referred to as full-reference IQA. As another example, image assessments can be performed based on comparison to statistics generated from the original image used as a reference, which is sometimes referred to as reduced-reference IQA. As yet another example, image assessments can be performed without any comparison to an original image, which is sometimes referred to as no-reference IQA.

The mechanisms described herein for selectively presenting images captured by confocal laser endomicroscopy can generally be described as objective no-reference IQA techniques. Many existing objective no-reference IQA techniques have three stages: measurement of features, pooling these features in time and/or space, and mapping the pooling analysis results to an estimation of the perceived quality. The features analyzed can be an estimation of one specific artifact considering a given model of that degradation (e.g., blur) or a distortion-generic estimation of overall quality of the image.

Providing a real time (or near-real time) diagnostic value assessment of images (e.g., fast enough to be used during the surgical acquisition process and accurate enough for the pathologist to rely on) to automatically detect diagnostic frames is desirable to streamline the analysis of images and filter useful images from non-useful images for the pathologist/surgeon. The mechanisms described herein can be used to automatically classify images as diagnostic or non-diagnostic.

In some embodiments, the mechanisms described herein can use convolutional neural networks ("CNN"s) to classify the CLE images acquired from brain tumors during surgery. A training dataset can be defined using a subjective assessment performed, at least in part, by human experts (e.g., pathologists) to classify each image in a set of CLE images of brain tissue as diagnostic or non-diagnostic. In some embodiments, this training dataset can be used to train one or more CNNs. For example, the training dataset can be divided into a training portion used to train the CNN, a validation portion used to determine the accuracy of the CNN during the training phase, and a test portion used to test the CNN's performance on novel images.

In some embodiments, any suitable CNN can be trained to determine whether images are diagnostic or non-diagnostic. For example, a CNN model based on the AlexNet CNN described in Krizhevsky, A., et al., "ImageNet classification with deep convolutional neural networks," *Advances in neural information processing systems*, pp. 1097-1105 (2012) ("AlexNet"), can be trained to differentiate diagnostic images from non-diagnostic images in accordance with the mechanisms described herein using a threshold of 0.5. As another example, another CNN model based on AlexNet ("AlexNet II") can be trained to differentiate diagnostic images from non-diagnostic images in accordance with the mechanisms described herein using a threshold of 0.00001. As yet another example, a CNN model based on the GoogLeNet CNN described in Szegedy, C., et al., "Going deeper with convolutions," *Proceedings of the IEEE conference on Computer Vision and Pattern Recognition*, pp. 1-9 (2015) ("GoogLeNet") can be trained to differentiate diagnostic images from non-diagnostic images in accordance with the mechanisms described herein using a threshold of 0.5. As still another example, another CNN model based on GoogLeNet ("GoogLeNet II") can be trained to differentiate diagnostic images from non-diagnostic images in accordance with the mechanisms described herein using a threshold of 0.00001. In these examples, the CNN models can sort diagnostic images from non-diagnostic images in real-time. Krizhevsky et al. and Szegedy et al. are each hereby incorporated by reference herein in their entirety.

Automatic differentiation of diagnostic images from non-diagnostic images for further analysis can save time for clinicians, and may be able to suggest tumor type during image acquisition to guide a neurosurgeon in making a timely decision, which could facilitate shorter and more precise surgeries.

Figure 3:
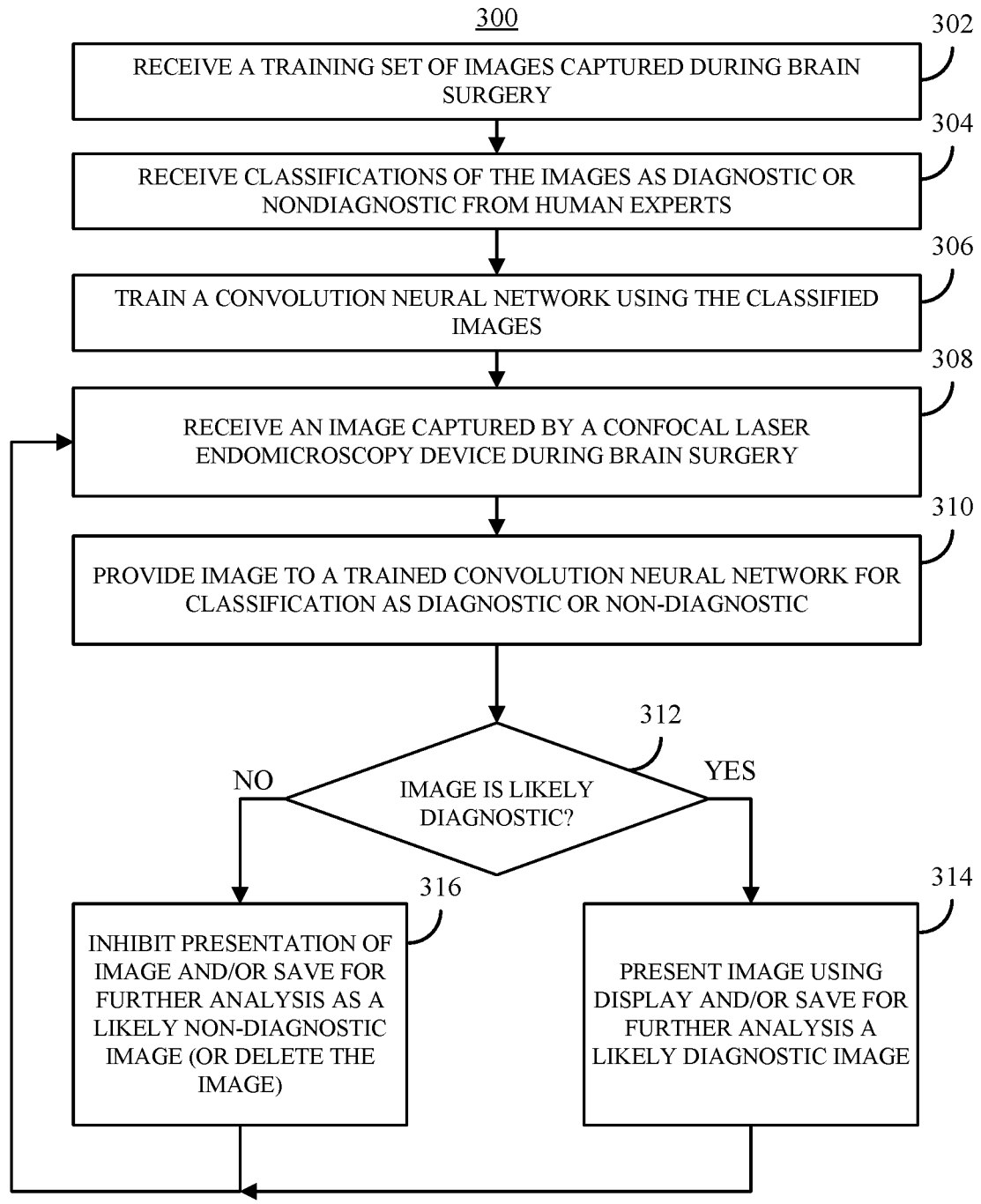
FIG. 3 shows an example of a process for selectively presenting images captured by confocal laser endomicroscopy in accordance with some embodiments of the disclosed subject matter.

FIG. 3 shows an example of a process 300 for selectively presenting images captured by confocal laser endomicroscopy in accordance with some embodiments of the disclosed subject matter. As shown in FIG. 3, at 302, process 300 can receive a set of training images captured during brain surgery. The training set of images can be assembled using any suitable procedure. For example, in some embodiments, the images can be captured using any suitable confocal laser endomicroscopy device during brain surgery. In a more particular example, in some embodiments, at least a portion of the images can be images captured using the OPTISCAN FIVE1 CLE device initially available from OPTISCAN IMAGING LTD. of Melbourne, Australia, which can include a handheld, miniaturized optical laser scanner having a rigid probe with a 6.3 millimeters (mm) outer diameter and a working length of 150 mm. A 488 nanometer (nm) diode laser can provide incident excitation light, and fluorescent emission can be detected at 505-585 nm using a band-pass filter via a single optical fiber acting as both the excitation pinhole and the detection pinhole for confocal isolation of the focal plane. The detector signal can be digitized synchronously with the scanning to construct images parallel to the tissue surface (sometimes referred to as en face optical sections). Note that use of the OPTISCAN FIVE1 is merely an example, and any suitable CLE device can be used to capture images during brain surgery, such as the CONVIVO CLE device available from CARL ZEISS AG of Oberkochen, Germany, or the CELLVIZIO device available from Mauna Kea Technologies of Paris, France.

In some embodiments, laser power can be set to 550-900 microwatts (μW) at brain tissue, with maximum power limited to 1000 μW. A field of view of 475×475 μm (approximately 1000× magnification on a 21-inch screen) can be scanned either at 1024×512 pixels (0.8/second frame rate) or at 1024×1024 pixels (1.2/second frame rate), with a lateral resolution of 0.7 μm and an axial resolution (i.e., effective optical slice thickness) of approximately 4.5 μm. Note that these frame rates are a specific example, and higher frame rates can be achieved by capturing images at lower resolution, and some CLE devices may be capable of capturing images with the same or higher resolution at the same frame rate or more. In either case, this would result in even more images being generated when the CLE device is used for the same length of time.

The resulting images can be stored digitally and/or can be recorded as a time-lapse series. During the procedure, a foot pedal can be provided to control the variable confocal imaging plane depth at which images are captured. For example, images can be captured at a depth of 0-500 μm from the surface of the tissue. In a more particular example, in vivo images can be captured intraoperatively during the removal of a brain tumor approximately five minutes after intravenous injection of 5 mL of a 10% FNa solution. Note that this is merely an example and FNa can be administered in other amounts. For example, the amount of FNa that is administered can be from 1 milligram (mg) per kilogram (kg) to 20 mg/kg, and in some cases can be administered repeatedly during a single procedure.

In some embodiments, images can be obtained using the CLE probe affixed to a Greenberg retractor arm. In such embodiments, the retractor can be tightened to a degree that facilitates both smooth movement and steady operation. The probe can be moved gently, without losing contact, along the surface of the tissue to obtain images from several biopsy locations. In some embodiments, co-registration of the probe with the image guided surgical system can be used to determine precise intraoperative localization of the CLE imaging with the site of the biopsy. The images captured for the training set can include normal brain regions and regions of obvious tumor, in addition to transitional zones between what appeared to be normal brain and tumor. Images can further be acquired from each biopsy location.

Additionally, in some embodiments, in combination with in vivo imaging of multiple locations within the resection bed with CLE, tissue samples (approximately 0.5 cm$^3$) can be harvested from each patient during the procedure to be examined ex vivo. For example, tissue samples suspicious for tumor can be harvested from the surgical field and imaged on a separate work station away from the patient, but within the operating room. In such an example, additional fluorophore beyond the FNa given intravenously is not used, which can more closely replicate the conditions under which tissue was imaged in vivo. Multiple images can be obtained from each biopsy location. Additionally, areas that were imaged using CLE ex vivo can be marked with tissue ink so that precise locations can be validated with conventional histology. For example, the diagnosis based on the image can be validated based on lab results at the same locations, which can help when classifying an image in the test set as a diagnostic or non-diagnostic image (e.g., if the pathologist made an incorrect diagnoses based on the image, that may indicate that the image was non-diagnostic, even if a human expert indicated that it was diagnostic).

At 304, process 300 can receive classifications of images in the test set as being either diagnostic or non-diagnostic images from data generated by human experts reviewing the images. For example, the images received at 302 can be reviewed by a neuropathologist(s) and/or neurosurgeon(s), who can each make a determination of whether each image reviewed can be used to make a diagnosis or if it cannot be used to make a diagnosis. In a more particular example, the CLE images can be compared with both frozen and permanent histological sections by a neuropathologist and 2 neurosurgeons who were not involved in the surgeries. For each case, the experts can analyze the histopathological features of corresponding CLE images and H & E-stained frozen and permanent sections. The human experts can classify each image as diagnostic (i.e., the confocal images revealed identifiable histological features) or as non-diagnostic (i.e., the image did not provide enough identifiable histological features due to distortion by blood artifact, motion artifacts, or any other reason).

At 306, process 300 can train one or more CNNs using the classified images. In some embodiments, process 300 can use any suitable procedure for training the CNN. In general, a CNN is a multilayer learning framework, which can include an input layer, a series of convolutional layers and an output layer. The CNN is designed to learn a hierarchy of feature representations. Response maps in each layer can be convolved with a number of filters and further down-sampled by pooling operations. These pooling operations can aggregate values in a smaller region by any suitable down-sampling functions including selecting the maximum of the values in the region, selecting the minimum of the values in the region, and averaging the values in the region. In a more particular example, the softmax loss function can be used which is given by:

$$L(t, y) = -\frac{1}{N} \sum_{n=1}^{N} \sum_{k=1}^{C} t_k^n \log\left(\frac{e^{y_k^n}}{\sum_{m=1}^{C} e^{y_m^n}}\right) \quad (1)$$

where $t_k^n$ is the $n^{th}$ training example's $k^{th}$ ground truth output, and $y_k^n$ is the value of the $k^{th}$ output layer unit in response to the n-th input training sample. N is the number of training samples, and since two categories are considered (i.e., diagnostic and non-diagnostic), C=2. In some embodiments, learning in a CNN can be based on Stochastic Gradient Descent ("SGD"), which includes two main operations: Forward Propagation and Back Propagation. The learning rate can be dynamically lowered as training progresses.

In some embodiments, as described in more detail below, process 300 can use a portion of the training set as positive and negative examples that are input to the CNN being trained. In such an example, a second portion of the images can be used to verify the accuracy of the CNN as it is being trained. A third portion can be used to test the CNN after it is trained to independently evaluate the accuracy of the CNN-based model with novel images (i.e., images that were not to train the CNN).

In some embodiments, any suitable type of CNN can be used. For example, a CNN with five convolutional layers based on AlexNet can be trained using the training set. Such a CNN can start with an input layer that receives a resized version of the original image if the resolution of the original image is higher than a threshold. In a more particular example, original images that are 1024×1024 pixels can be reduced to 256×256 pixel images. After the input layer, two pairs of convolutional and pooling layers can be used. In each convolutional layer multiple kernels can be convolved with different areas of previous layer output (receptive field) with the result progressing through a nonlinear activation function and normalization (e.g., using a rectified linear unit ("RLU")) to create the output of that layer.

In some embodiments, the convolutional layers can extract many features from the image data, while minimizing parameter numbers, partially by using the same kernel over the entire image for each following plane. Output from each convolutional layer can then be fed to the next pooling layer, which can replace the output of each location in the previous plane with a summary of the surrounding pixels (e.g., an AlexNet-based CNN can use maximum pooling). In some embodiments, pooling layers can reduce the effect of small translations in the image data on the output of the network.

After two convolution-pooling combinations, the output of the last pooling layer can be inputted to a third convolution layer, which can be followed by two other convolution layers (e.g., layers 6-8) and one final pooling layer (e.g., layer 9). The output of the 9th layer can be fed to a fully connected layer which then feeds 4096 neurons of the next fully connected layer. The last fully connected layer can be followed by an output layer, which gives the ultimate result of classification.

Figure 4:
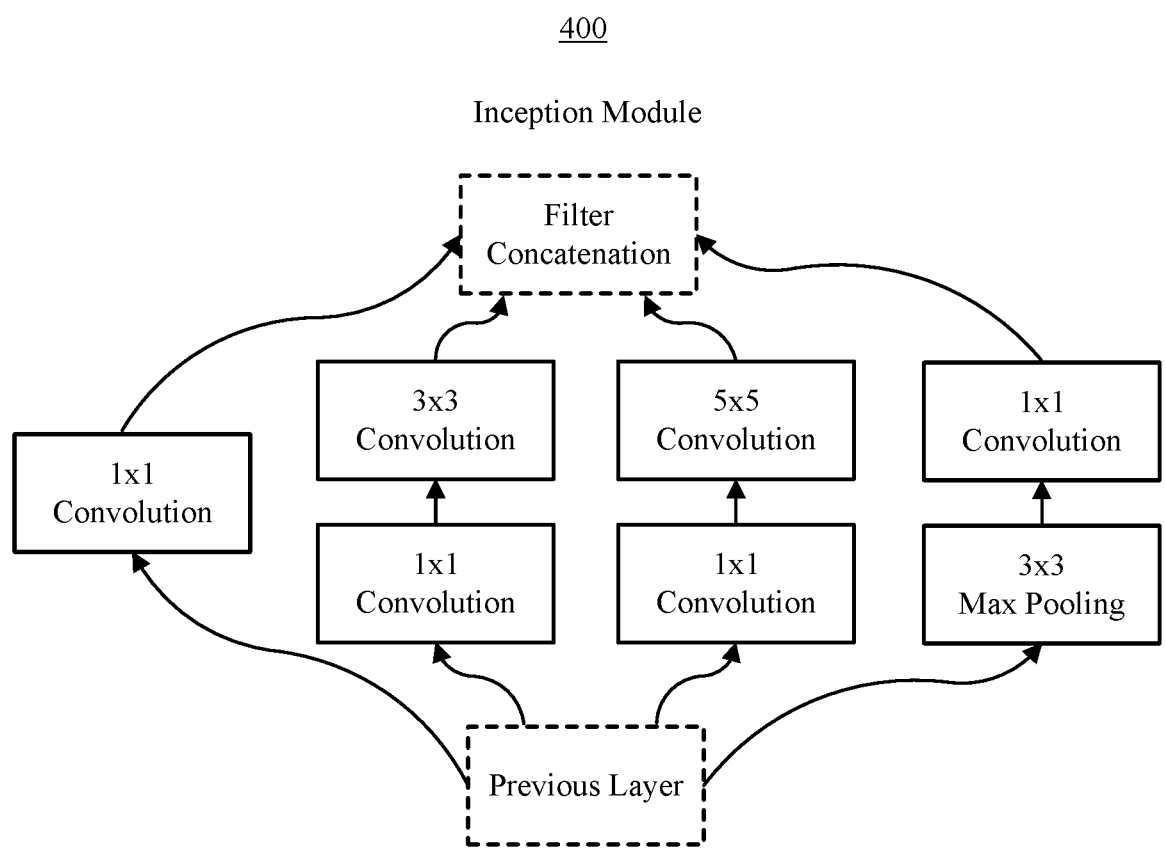
FIG. 4 shows an example of an inception module.

As another example, a CNN with twenty two total layers, and nine inception modules based on GoogLeNet can be trained with the training data. In such a CNN, each inception module can be a combination of filters of size 1×1, 3×3, and 5×5 convolution layers, and a 3×3 max pooling layer connected in parallel with output filter banks concatenated into a single vector as the input for next stage. An example of an inception module is shown in FIG. 4.

At 308, process 300 can receive an image captured by a CLE device during brain surgery. In some embodiments, the received image can be in any suitable format, and may need to be converted to another format. For example, the image can be converted from a received 1024×1024 pixel image to a 256×256 pixel image. In some embodiments, the image can be received from any suitable source. For example, the image can be received from the CLE device (e.g., over a wired or wireless connection). As another example, the image can be received from another device (e.g., a computing device coupled to the CLE device).

At 310, process 300 can provide the image (after any necessary preprocessing) to the CNN trained at 306 for classification as a diagnostic image or a non-diagnostic image. In some embodiments, the CNN can be executed by any suitable computing device. For example, the computing device that received the image at 308 can also execute the CNN. As another example, the CNN can be executed by another computing device (e.g., a server).

At 312, process 300 can receive an output from the CNN that is indicative of the likelihood that the image can be used for diagnostic purposes or not (i.e., the likelihood that the image is diagnostic). For example, the output of the CNN can encode the probability that the image is likely to be useful in diagnosing whether tissue in the image is normal tissue or tissue from a tumor. In some embodiments, process 300 and/or the CNN can use any suitable threshold for determining whether an image is likely to be diagnostic. If process 300 determines, based on the output of the CNN, that the image is likely (to at least a threshold probability) to be diagnostic ("YES" at 312), process 300 can move to 314 and present the image (e.g., using a display coupled to the CLE device and/or a device executing process 300) and/or save the image as a diagnostic image for later analysis. Otherwise, if process 300 determines, based on the output of the CNN, that the image is not likely to be diagnostic ("NO" at 312), process 300 can move to 316 and inhibit presentation of the image (e.g., not display the image, delete the image from memory, flag the image as non-diagnostic in memory, etc.). In some embodiments, the image can be saved as an image that is likely a non-diagnostic image. Alternatively, in some embodiments the image can be deleted (e.g., based on the likelihood that the image is non-diagnostic). Process 300 can return to 308 and receive a next image from 314 or 316.

Figure 5:
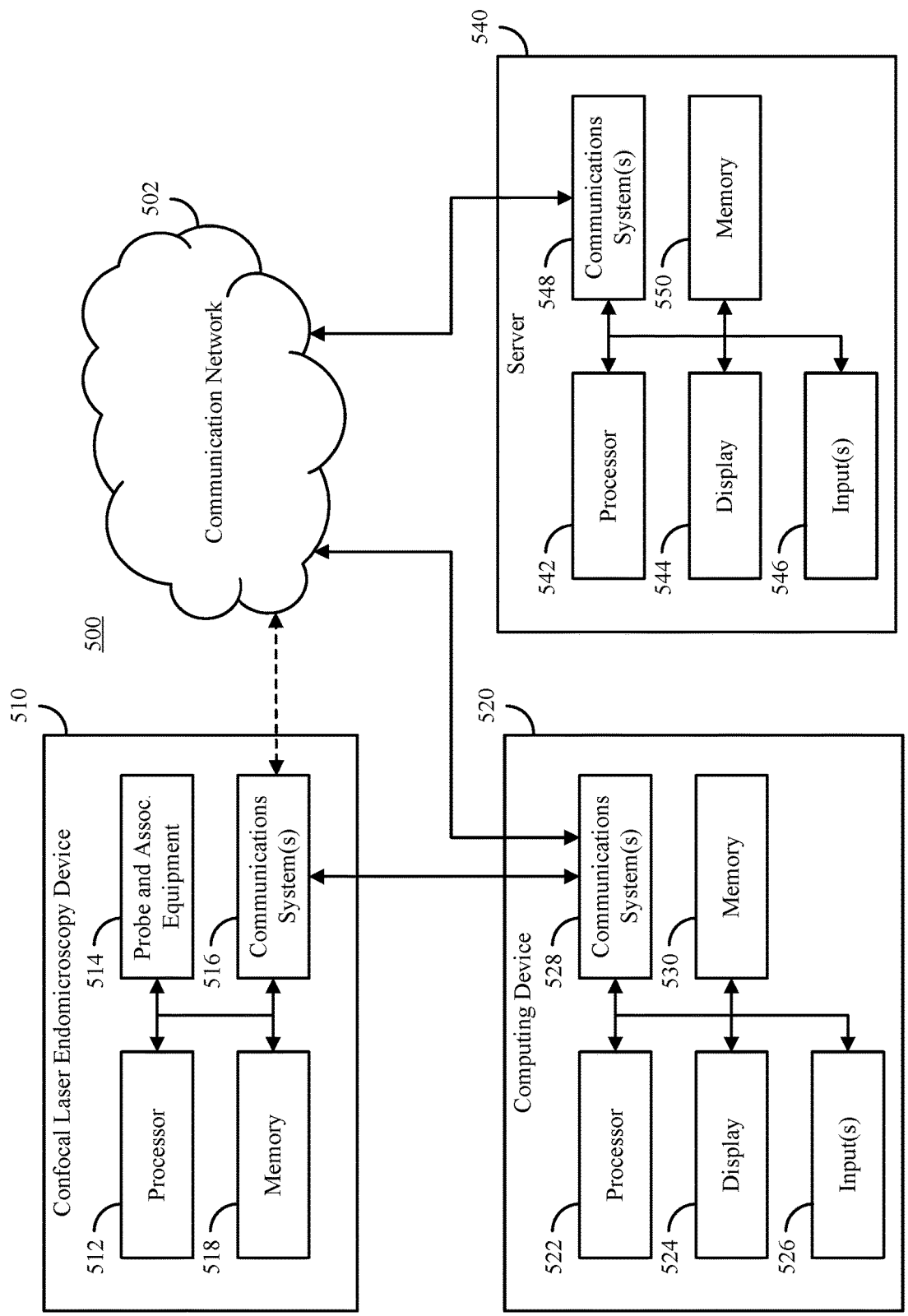
FIG. 5 shows an example of hardware that can be used to implement a confocal laser endomicroscopy device, a computing device, and a server in accordance with some embodiments of the disclosed subject matter.

FIG. 5 shows an example 500 of hardware that can be used to implement a confocal laser endomicroscopy device 510, a computing device 520 and a server 540 in accordance with some embodiments of the disclosed subject matter. As shown in FIG. 5, in some embodiments, CLE device 510 can include a processor 512, a probe and associated equipment (e.g., a laser, a fiber optic cable, etc.) 514, one or more communication systems 516, and/or memory 518. In some embodiments, processor 512 can be any suitable hardware processor or combination of processors, such as a central processing unit, a graphics processing unit, etc. In some embodiments, communications system(s) 516 can include any suitable hardware, firmware, and/or software for communicating information to computing device 520, over communication network 502 and/or any over other suitable communication networks. For example, communications systems 516 can include one or more transceivers, one or more communication chips and/or chip sets, etc. In a more particular example, communications systems 526 can include hardware, firmware and/or software that can be used to communicate data over a coaxial cable, a fiber optic cable, an Ethernet connection, a USB connection, to establish a Wi-Fi connection, a Bluetooth connection, a cellular connection, etc.

In some embodiments, memory 518 can include any suitable storage device or devices that can be used to store instructions, values, etc., that can be used, for example, by processor 512 to control operation of probe 514, to communicate with computing device 520 and/or server 540 via communications system(s) 516, etc. Memory 518 can include any suitable volatile memory, non-volatile memory, storage, or any suitable combination thereof. For example, memory 518 can include RAM, ROM, EEPROM, one or more flash drives, one or more hard disks, one or more solid state drives, one or more optical drives, etc. In some embodiments, memory 518 can have encoded thereon a computer program for controlling operation of CLE device 510. In such embodiments, processor 512 can execute at least a portion of the computer program to capture images of tissue via probe 514.

In some embodiments, computing device 520 can include a processor 522, a display 524, one or more inputs 526, one or more communication systems 528, and/or memory 530. In some embodiments, processor 522 can be any suitable hardware processor or combination of processors, such as a central processing unit, a graphics processing unit, etc. In some embodiments, display 524 can include any suitable display devices, such as a computer monitor, a touchscreen, a television, etc. In some embodiments, inputs 526 can include any suitable input devices and/or sensors that can be used to receive user input, such as a keyboard, a mouse, a touchscreen, a microphone, etc.

In some embodiments, communications systems 528 can include any suitable hardware, firmware, and/or software for communicating with CLE device 510, for communicating information over communication network 502 (e.g., to and/or from server 540), and/or for communicating over any other suitable communication networks. For example, communications systems 528 can include one or more transceivers, one or more communication chips and/or chip sets, etc. In a more particular example, communications systems 528 can include hardware, firmware and/or software that can be used to establish a coaxial connection, a fiber optic connection, an Ethernet connection, a USB connection, a Wi-Fi connection, a Bluetooth connection, a cellular connection, etc.

In some embodiments, memory 530 can include any suitable storage device or devices that can be used to store instructions, values, etc., that can be used, for example, by processor 522 to present content using display 524, to communicate with one or more CLE devices 510, to communicate with server 540, etc. Memory 530 can include any suitable volatile memory, non-volatile memory, storage, or any suitable combination thereof. For example, memory 530 can include RAM, ROM, EEPROM, one or more flash drives, one or more hard disks, one or more solid state drives, one or more optical drives, etc. In some embodiments, memory 530 can have encoded thereon a computer program for controlling operation of computing device 520. In such embodiments, processor 522 can execute at least a portion of the computer program to receive a training set of images, train a CNN, classify images from the CLE device 510 using the trained CNN, etc. For example, processor 522 can execute one or more portions of process 300. In some embodiments, computing device 520 can be any suitable computing device, such as a personal computer, a laptop computer, a tablet computer, a smartphone, a server, etc.

In some embodiments, server 540 can include a processor 542, a display 544, one or more inputs 546, one or more communication systems 548, and/or memory 530. In some embodiments, processor 542 can be any suitable hardware processor or combination of processors, such as a central processing unit, a graphics processing unit, etc. In some embodiments, display 544 can include any suitable display devices, such as a computer monitor, a touchscreen, a television, etc. In some embodiments, inputs 546 can include any suitable input devices and/or sensors that can be used to receive user input, such as a keyboard, a mouse, a touchscreen, a microphone, etc.

In some embodiments, communications systems 548 can include any suitable hardware, firmware, and/or software for communicating information over communication network 502 (e.g., with CLE device 510, computing device 520, etc.), and/or for communicating over any other suitable communication networks. For example, communications systems 548 can include one or more transceivers, one or more communication chips and/or chip sets, etc. In a more particular example, communications systems 548 can include hardware, firmware and/or software that can be used to establish a coaxial connection, a fiber optic connection, an Ethernet connection, a USB connection, a Wi-Fi connection, a Bluetooth connection, a cellular connection, etc.

In some embodiments, memory 550 can include any suitable storage device or devices that can be used to store instructions, values, etc., that can be used, for example, by processor 542 to present content using display 544, to communicate with one or more CLE devices 510, to communicate with one or more computing device 520, etc. Memory 550 can include any suitable volatile memory, non-volatile memory, storage, or any suitable combination thereof. For example, memory 550 can include RAM, ROM, EEPROM, one or more flash drives, one or more hard disks, one or more solid state drives, one or more optical drives, etc. In some embodiments, memory 550 can have encoded thereon a server program for controlling operation of server 540. In such embodiments, processor 542 can execute at least a portion of the server program to receive a training set of images, train a CNN, classify images from the CLE device 510 using the trained CNN, etc. For example, processor 542 can execute one or more portions of process 300. In some embodiments, server 540 can be any suitable computing device or combination of devices, such as a server computer, a distributed computing system, a personal computer, a laptop computer, a tablet computer, a smartphone, etc.

In some embodiments, communication network 502 can be any suitable communication network or combination of communication networks. For example, communication network 502 can be a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, etc. Communications links shown in FIG. 5 can each be any suitable communications link or combination of communications links, such as wired links, fiber optic links, Wi-Fi links, Bluetooth links, cellular links, etc.

Figures 6A, 6B:
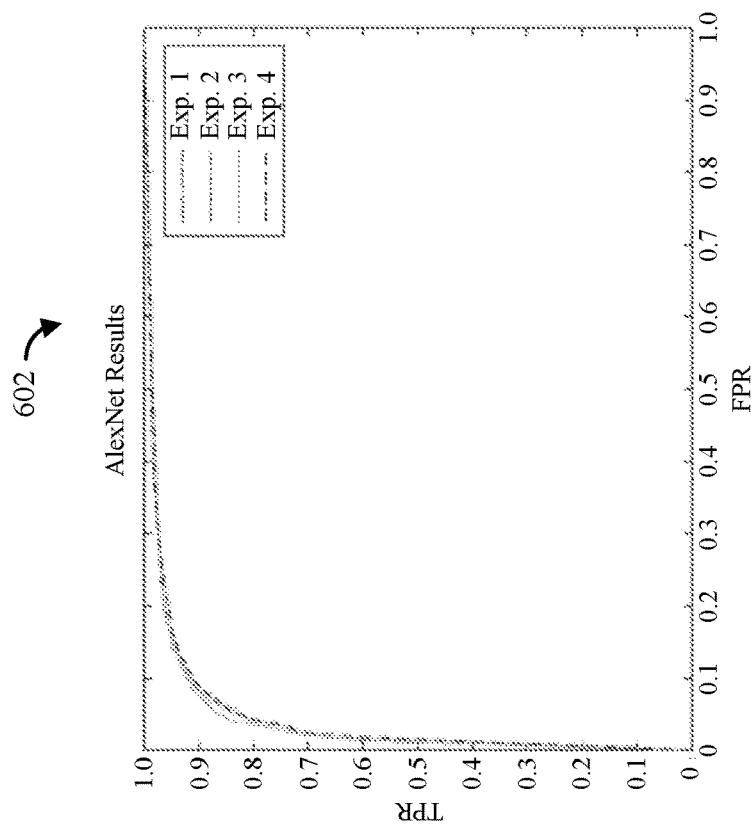
FIG. 6A shows a plot comparing the performance of AlexNet-based CNNs trained in accordance with some embodiments of the disclosed subject matter using different batches of images from a training dataset.
FIG. 6B shows a plot comparing the performance of GoogLeNet-based CNNs trained in accordance with some embodiments of the disclosed subject matter using different batches of images from a training dataset.

FIGS. 6A and 6B show examples of results obtained by training two different CNNs as described herein on a set of classified images. FIG. 6A shows results 602 of testing a CNN referred to as an AlexNet-based CNN that was trained using images from a dataset that included 16,795 images obtained from 74 CLE-aided brain tumor surgery patients, which were classified by experts (i.e., a neuropathologist and 2 neurosurgeons) into 8572 non-diagnostic images and 8223 diagnostic images. The ground truth for all the images was provided by pathologists determining whether each image was a diagnostic image or a non-diagnostic image. FIG. 6B shows results 604 of testing a CNN referred to as a GoogLeNet-based CNN that was trained using images from the same dataset of 16,795 images.

Both CNNs (i.e., the AlexNet-based CNN and the GoogLeNet-based CNN described above) were evaluated using a 4-fold cross validation. In each experiment (sometimes referred to as a fold), 25% of images were set apart as test images for evaluation of model. One fourth of the remaining 75% (i.e., 18.75%) of images were set apart for validation of the models during training, and the remaining (56.25%) of the images were used to train the model (as shown in Table 1). In the experiments, to avoid overfitting the model, the training process was stopped after validation accuracy failed to further increase or when loss on validation images was increasing. The trained models were then used to evaluate the test images that were set aside to evaluate the model accuracy, specificity and sensitivity. In the experiments used to generate the results in FIGS. 6A and 6B, a GeForce GTX 980 TI (6 GB) GPU from NVIDIA was used during training and testing of the CNNs.

TABLE 1

| Phase | Train | | Validation | | Test | |
|---|---|---|---|---|---|---|
| Experiment | Diag | Nondiag | Diag | Nondiag | Diag | Nondiag |
| Fold 1 | 4626 | 4822 | 1542 | 1607 | 2055 | 2143 |
| Fold 2 | 4625 | 4822 | 1542 | 1607 | 2056 | 2143 |
| Fold 3 | 4625 | 4822 | 1542 | 1607 | 2056 | 2143 |
| Fold 4 | 4625 | 4822 | 1542 | 1607 | 2056 | 2143 |

In these experiments, four common evaluation metrics were used: accuracy, sensitivity, specificity and area under the receiver operating characteristics ("ROC") curve ("AUC"). In these results, the state of being a diagnostic image is assumed as positive and the state of being non-diagnostic is assumed as negative. Making opposite assumptions would not change the results, but would produce the opposite values for sensitivity and specificity. As described herein, sensitivity indicates the model's ability to correctly classify diagnostic images as diagnostic images and is also sometimes referred to as the true positive rate ("TPR"). Specificity indicates the model's ability to correctly classify non-diagnostic images as non-diagnostic images. Accuracy indicates the model's ability at correctly classifying both diagnostic and non-diagnostic images.

Each ROC curve in FIGS. 6A and 6B shows the TPR versus false positive rate ("FPR"), or equivalently, sensitivity versus (1−specificity), for different thresholds of the classifier output. In order to use a scalar value representing the classifier performance, the AUC can be used. The AUC of a classifier is equivalent to the probability that the classifier will rank a randomly chosen positive instance higher than a randomly chosen negative instance.

Training the AlexNet-based CNN required about 2 hours for each fold and prediction time on the test images (4199 images) was about 44 s total (~95 images/second). Results for each experiment are shown in Table 2, below. On average, the AlexNet-based models exhibited 90.79% accuracy, 90.71% sensitivity and 90.86% specificity on the test images.

In order to evaluate the reliability of the model, ROC analysis was performed on the results from each experiment and AUC was calculated (as shown below in Table 2). FIG. 6A shows the ROC curve obtained from each fold of this experiment for the AlexNet-based model. The model prediction for each image, probability of being diagnostic or non-diagnostic and the ground truth from subjective assessment was used to perform ROC analysis in MATLAB. The same process was done for all the subsequent experiments when doing ROC analysis. The average AUC was 0.9583 in this experiment.

TABLE 2

| Exp (#) | Accuracy (%) | Sensitivity (%) | Specificity (%) | AUC |
|---|---|---|---|---|
| 1 | 91.35 | 90.8 | 91.88 | 0.9607 |
| 2 | 90.69 | 91.25 | 90.15 | 0.9583 |
| 3 | 90.66 | 90.76 | 90.57 | 0.9584 |
| 4 | 90.45 | 90.03 | 90.85 | 0.9556 |
| Mean | 90.79 | 90.71 | 90.86 | 0.9583 |

Training the GoogLeNet-based CNN network required about 9 hours for each fold and prediction time on the test images (4199 images) was about 50 s total (~84 images/second). Results for each experiment are shown below in Table 3. On average, the GoogLeNet-based models exhibited 90.74% accuracy, 90.80% sensitivity and 90.67% specificity on test images. FIG. 6B shows the ROC curve obtained from each fold of this experiment for the GoogLeNet-based model. The average AUC was 0.9553 in this experiment.

TABLE 3

| Exp (#) | Accuracy (%) | Sensitivity (%) | Specificity (%) | AUC |
|---|---|---|---|---|
| 1 | 90.79 | 92.11 | 89.78 | 0.9545 |
| 2 | 90.45 | 88.33 | 92.66 | 0.9561 |
| 3 | 90.78 | 92.16 | 89.35 | 0.9556 |
| 4 | 90.76 | 90.62 | 90.90 | 0.9551 |
| Mean | 90.74 | 90.80 | 90.67 | 0.9553 |

The images were also evaluated using an entropy-based model as a reference to compare the classification performance of the CNN-based models. Entropy is sometimes used as a measure of the information content of in an image.

The entropy of all images was calculated and normalized between 0 and 1 using MATLAB. The normalized entropy of an image can indicate the probability of the image being informative. For example, in general, an image with higher entropy tends to be more informative than an image with lower entropy, when evaluated subjectively.

Figure 7:
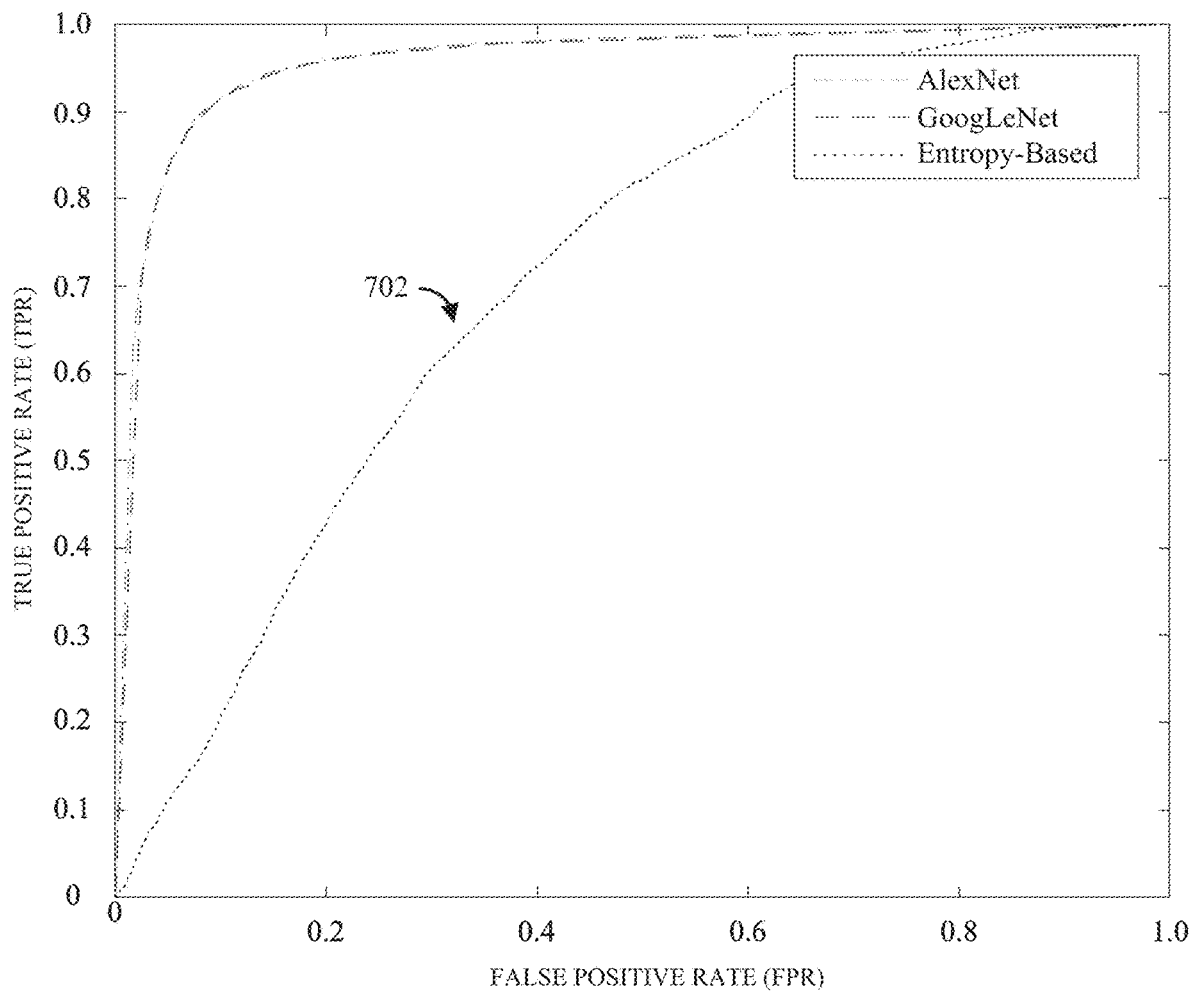
FIG. 7 shows a plot comparing the performance of CNNs trained in accordance with some embodiments of the disclosed subject matter and an entropy-based model.

The model prediction for each image, probability of being informative and the ground truth from subjective assessment was used to perform ROC analysis in MATLAB. Table 4 shows the model performance of all of the models evaluated, including the entropy-based model. FIG. 7 shows the average ROC curve for the AlexNet-based CNN, the GoogLeNet-based CNN, and the entropy-based model 702 achieved from this experiment.

TABLE 4

| Model | Accuracy (%) | Sensitivity (%) | Specificity (%) | AUC |
|---|---|---|---|---|
| AlexNet | 90.79 | 90.71 | 90.86 | 0.9583 |
| GoogLeNet | 90.74 | 90.80 | 90.67 | 0.9553 |
| AlexNet II | 75.95 | 98.42 | 54.40 | 0.9583 |
| GoogLeNet II | 79.75 | 97.91 | 62.33 | 0.9553 |
| Entropy-based | 57.20 | 98.20 | 17.87 | 0.7122 |

In some embodiments, the mechanisms described herein can train one or more CNNs that have not been pre-trained using CLE images labeled as diagnostic and non-diagnostic (sometimes referred to herein as training from scratch). Additionally or alternatively, the mechanisms described herein can perform additional training to a CNN that has been pretrained to recognize general objects (e.g., based on the ImageNet database). For example, the mechanisms can perform additional training on certain layers of the pre-trained CNN (sometimes referred to herein as shallow fine-tuning). As another example, the mechanisms can perform additional training on many layers of the pretrained CNN (sometimes referred to herein as deep fine-tuning). As described below, with a limited number of labeled images in a dataset, shallow fine-tuning can perform better than training from scratch, but deep fine-tuning can perform better than both shallow fine-tuning can perform better than training from scratch.

In some embodiments, the mechanisms described herein can train multiple CNNs to classify CLE images as diagnostic or non-diagnostic, and for each image, each of the CNNs can classify the image as diagnostic or non-diagnostic, and the classifications from the multiple CNNs can be combined to classify that image. Combining the outputs of multiple models is sometimes referred to herein as ensemble modeling. Ensemble modeling can improve performance and reduce variance.

While CNNs that are trained to recognize relatively common objects (e.g., dogs, bicycles, cars, etc.), are often trained using tens of thousands to millions of labeled examples of these objects, the number of images used for deep learning applications in medical imaging is usually much smaller (e.g., because labeling such images requires the time of a highly trained person, such as a pathologist). In some embodiments, transfer learning can be used to attempt to overcome the relatively small size of the training images available. For example, a portion of a CNN trained on a large image dataset of common objects (e.g., ImageNet) can be used as feature extractor. As another example, a CNN can be trained with parameters (e.g., weights and/or biases) initialized to values from a CNN trained on a large image dataset of common objects (e.g., ImageNet), rather than initializing the parameters randomly.

In some embodiments, diversity can be introduced into various CNNs that form an ensemble model by training different CNNs using different subsets of data from the dataset of images (which is sometimes referred to as cross-validation). Although previous studies tried to create variant deep learning models by using different network architectures, none had employed training data diversification through cross-validation.

Potentially used at any time during a surgery, CLE interrogation of tissue generates images at a rate of approximately 0.8-1.2 frames per second. As described above, an image can be considered non-diagnostic when the histological features are obscured (e.g., by red blood cells, motion artifacts), are out of focus, and/or not abundant enough to provide useful information (e.g., histological features are only spares or absent). Acquired images can be exported from a CLE instrument as JPEG or TIFF files. In an example conventional procedure, a pathologist reviews all images that are captured (i.e., diagnostic and non-diagnostic images) to identify frames that are useful for diagnosis, and to explore those diagnostic frames in order to make a diagnosis. However, manual selection and review of thousands of images acquired during surgery by a CLE operator is tedious and impractical for widespread use.

As discussed above in connection with FIG. 3, a CNN can include many layers, such as convolutional layers, activation layers, pooling layers, etc. In some embodiments, convolutional layers can be used as a substitute for manually defined feature extractors. At each convolutional layer three dimensional matrices (kernels) are slid over the input and set the dot product of kernel weights with the receptive field of the input as the corresponding local output. This can help to retain the relative position of features to each other, and multi-kernel convolutional layers can prospectively extract several distinct feature maps from the same input image.

In some embodiments, output from a convolutional layer can be input into an activation function to adjust the negative values, such as a rectified linear unit (RLU). An RLU can be relatively simple compared to other activation functions, can be executed relatively quickly, can exhibit a reduced likelihood of vanishing gradients (especially in deep networks), and can often add sparsity over other nonlinear functions, such as sigmoid function. An RLU is sometimes referred to as an RLU layer. In some embodiments, a CNN can have any suitable number of RLU layers, and the output of $j^{th}$ RLU layer ($a_j^{out}$), given its input ($a_j^{in}$), can be calculated in-place (e.g., to consume less memory) in accordance with following:

$$a_j^{out} = \max(a_j^{in}, 0) \quad (2)$$

In some embodiments, a local response normalization (LRN) map (sometimes referred to herein as an LRN layer) can be present after the RLU layer in initial convolutional layers. An LRN layer can inhibit local RLU neurons' activations, since there's no bound to limit them in Equation 2. In some embodiments, an LRN can be implemented as described in Jia et al., "Caffe: Convolutional architecture for fast feature embedding," 2014, available at arXiv(dot)org with reference number 1408.5093, which is hereby incorporated herein by reference in its entirety. Using such an LRN, local regions can be expanded across neighbor feature maps at each spatial location. For example, the output of the $j^{th}$ LRN layer ($a_j^{out}$), given its input ($a_j^{in}$), can be calculated as:

$$a_j^{out} = \frac{a_j^{in}}{\left(1 + \frac{\alpha}{l}\sum_{n=1}^{L} a_j^{in}(n)^2\right)^{\beta}}, \quad (3)$$

where $a_j^{in}(n)$ is the $n^{th}$ element of the $a_j^{in}$ and L is the length of $a_j^{in}$ vector (i.e., the number of neighbor maps employed in the normalization), and $\alpha$, $\beta$ and L are the layer's hyperparameters, which can be set to values, such as, ($\alpha$=1, $\beta$=0.75 and L=5).

In some embodiments, after rectification (e.g., using an RLU layer) and normalization (e.g., using an LRN layer) of the convolutional layer output, the output can be further down-sampled by a pooling operation in a pooling layer, which can accumulate values in a smaller region by subsampling operations such as max, min, and average sampling. In some example implementations described below, max pooling was used in the pooling layers.

In some embodiments, following several convolutional and pooling layers, network lateral layers can be fully connected. In fully connected layers, each neuron of the layer's output is greedily connected to all the layer's input neurons, and can be characterized as a convolutional layer with a kernel size of the layer input. The layer output can also be passed through an RLU layer. In general, fully connected layers are often described as the classifier of a CNN, because they intake abstract features extracted in convolutional layers and generate an output as a prediction.

In some embodiments, fully connected layers are followed by a dropout layer, except the last fully connected layer that produces class-specific probabilities. In dropout layers, a subset of input neurons, as well as all their connections, can be temporarily removed from the network, which can reduce overfitting.

As described above in connection with FIG. 3, a CNN can be trained using Stochastic Gradient Descent, which can involve forward propagation and back propagation. In forward propagation, the model makes predictions using the images in the training batch and the current model parameters. After making a prediction for all training images, the loss can be calculated using the labels on the images (e.g., provided by experts in an initial review, as described below in connection with FIG. 9). In some embodiments, a softmax loss function can be represented by:

$$L(t, y) = -\frac{1}{N}\sum_{n=1}^{N}\sum_{k=1}^{C} t_k^n \log\left(\frac{e^{y_k^n}}{\sum_{m=1}^{C} e^{y_m^n}}\right), \quad (4)$$

where $t_k^n$ is the $n^{th}$ training image's $k^{th}$ ground truth output, and $y_k^n$ is the value of the $k^{th}$ output layer unit in response to the $n^{th}$ input training image. N is the number of training images in the minibatch, and with two diagnostic value categories, C=2.

Through back propagation, the loss gradient with respect to all model weights can be used to upgrade the weights in accordance with the following:

$$W(j, i+1) = W(j, i) + \mu\Delta W(j, i) - \alpha(j, i)\frac{\partial L}{\partial W(j)}, \quad (5)$$

where W (j, i), W (j, i+1) and $\Delta$W (j, i) are the weights of $j^{th}$ convolutional layer at iteration i and i+1 and the weight update of iteration i, $\mu$ is the momentum and $\alpha$(j, i) is the learning rate and is dynamically lowered as the training progresses.

Figure 8:
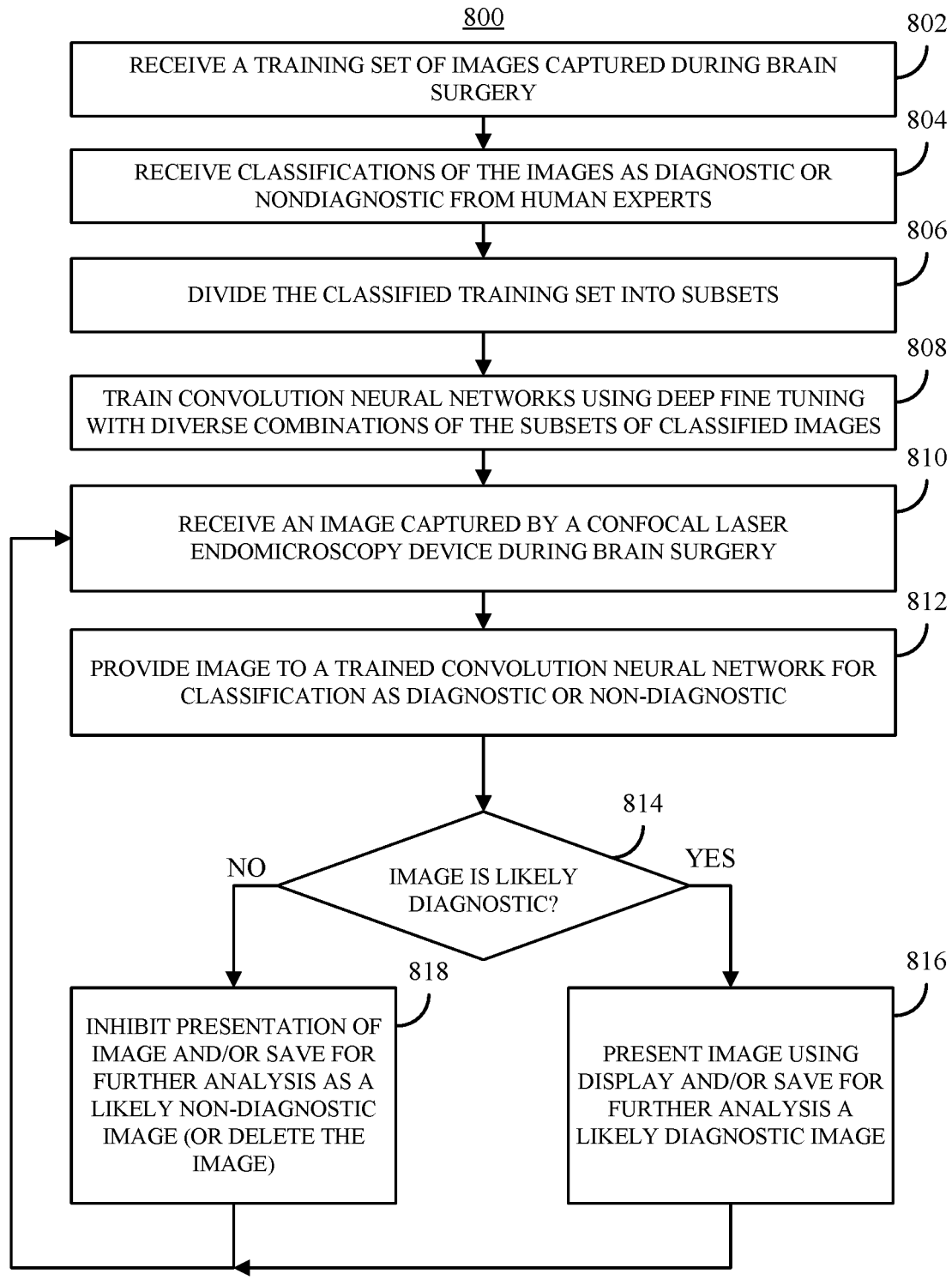
FIG. 8 shows an example of a process for selectively presenting images captured by confocal laser endomicroscopy using an ensemble of neural networks in accordance with some embodiments of the disclosed subject matter.

FIG. 8 shows an example 800 of a process for selectively presenting images captured by confocal laser endomicroscopy using an ensemble of neural networks in accordance with some embodiments of the disclosed subject matter. As shown in FIG. 8, at 802, process 800 can receive a set of training images captured during brain surgery. The training set of images can be assembled using any suitable procedure (e.g., as described above in connection with 302 of FIG. 3).

At 804, process 800 can receive classifications of images in the test set as being either diagnostic or non-diagnostic images from data generated by human experts reviewing the images (e.g., as described below in connection with FIG. 9).

At 806, process 800 can divide the classified images into subsets of images, which can be used in various combinations to train separate CNNs. For example, the classified images can be divided into a number of subsets equal to the number of CNNs to be used in an ensamble model. In a more particular example, the classified images can be divided into five subsets, and each of five CNNs can be trained using four of the five subsets such that each subset is omitted from one of the five CNNs.

At 808, process 800 can train multiple CNNs using different combinations of the subsets of classified images. In some embodiments, process 800 can use any suitable procedure for training the CNN, such as procedures described above in connection with FIG. 3 and/or Equations (2) to (5).

In some embodiments, as described above, the images in the subsets corresponding to a particular CNN can be divided into a training set, a validation set, and a test set. Additionally, as described below in connection with FIG. 9, the images corresponding to a particular CNN can be grouped by patient, such that all images associated with a particular patient are assigned to images used during training (e.g., the training set or validation set) or to images used during testing (e.g., the test set). In some embodiments, process 800 can use a portion of the training set as positive and negative examples that are input to the CNN being trained. In such an example, the validation set can be used to verify the accuracy of the CNN as it is being trained, and the test set can be used to test the CNN after it is trained to independently evaluate the accuracy of the CNN-based model with novel images (i.e., images that were not to train the CNN). In some embodiments, any suitable type of CNN can be used, such as an AlexNet-based CNN or a GoogLeNet-based CNN.

At 810, process 800 can receive an image captured by a CLE device during brain surgery. In some embodiments, the received image can be in any suitable format, and may need to be converted to another format. For example, the image can be converted from a received 1024×1024 pixel image to a 256×256 pixel image. In some embodiments, the image can be received from any suitable source. For example, the image can be received from the CLE device (e.g., over a wired or wireless connection). As another example, the image can be received from another device (e.g., a computing device coupled to the CLE device).

At 812, process 800 can provide the image (after any necessary preprocessing) to the CNNs trained at 806 for classification as a diagnostic image or a non-diagnostic image. In some embodiments, the CNNs can be executed by any suitable computing device. For example, the computing device that received the image at 810 can also execute the CNN. As another example, the CNN can be executed by another computing device (e.g., a server).

At 814, process 800 can receive an output from an ensemble of CNNs that is indicative of the likelihood that the image can be used for diagnostic purposes or not (i.e., the likelihood that the image is diagnostic). For example, each CNN can generate an output that encodes the probability that the image is likely to be useful in diagnosing whether tissue in the image is normal tissue or tissue from a tumor.

In some embodiments, the outputs from each of the CNNs can be combined using any suitable technique or combination of techniques. For example, the outputs can be combined using a linear operator or a log-linear operator. If $y_k^n(j)$ is the value of the $k^{th}$ output layer unit of the $j^{th}$ CNN model in response to the $n^{th}$ input test image, the linear and log-linear ensemble classifier output for the same input can be represented as:

$$Ens_{linear}^n = \underset{k}{\mathrm{argmax}} \sum_{j=1}^{l} y_k^n(j), \quad (6)$$

$$Ens_{log\text{-}linear}^n = \underset{k}{\mathrm{argmax}} \prod_{j=1}^{l} y_k^n(j), \quad (7)$$

where l is the number of CNN models combined to generate the ensemble models.

In some embodiments, process 800 can determine the output of the ensemble model by combining the outputs of the various different CNNs using any suitable technique or combination of techniques. For example, process 800 can calculate the arithmetic mean of the outputs to encode the probability that the image is diagnostic or non-diagnostic using any suitable threshold (e.g., if the arithmetic mean is equal to or greater than a threshold of 0.5, the image can be considered diagnostic). As another example, process 800 can calculate the geometric mean of the outputs to encode the probability that the image is diagnostic or non-diagnostic using any suitable threshold. As yet another example, rather than combining the output values, process 800 can combine the output classifications by classifying an image as diagnostic or non-diagnostic based on the number of models that classified the image as diagnostic. In a more particular example, if at least half of the CNNs classified the image as diagnostic it can be classified as diagnostic, and vice versa. In another more particular example, the image can be classified as diagnostic if and only if each of the CNNs classified the image as diagnostic.

In some embodiments, the threshold can be adjustable to allow a user to control the sensitivity of the classification. For example, if a surgeon wanted to be presented with images that are more likely to be diagnostic, the surgeon can adjust the threshold upward to require a higher confidence in order to selectively present a particular image (e.g., to 0.6, 0.75, 0.9, 0.99, 0.999, etc.).

If process 800 determines, based on the output of the CNNs, that the image is likely (to at least a threshold probability) to be diagnostic ("YES" at 814), process 800 can move to 816 and present the image (e.g., using a display coupled to the CLE device and/or a device executing process 800) and/or save the image as a diagnostic image for later analysis. Otherwise, if process 800 determines, based on the output of the CNNs, that the image is not likely to be diagnostic ("NO" at 814), process 800 can move to 818 and inhibit presentation of the image (e.g., not display the image, delete the image from memory, flag the image as non-diagnostic in memory, etc.). In some embodiments, the image can be saved as an image that is likely a non-diagnostic image. Alternatively, in some embodiments the image can be deleted (e.g., based on the likelihood that the image is non-diagnostic). Process 800 can return from 814 or 816, to 810 and receive a next image.

Figure 9:
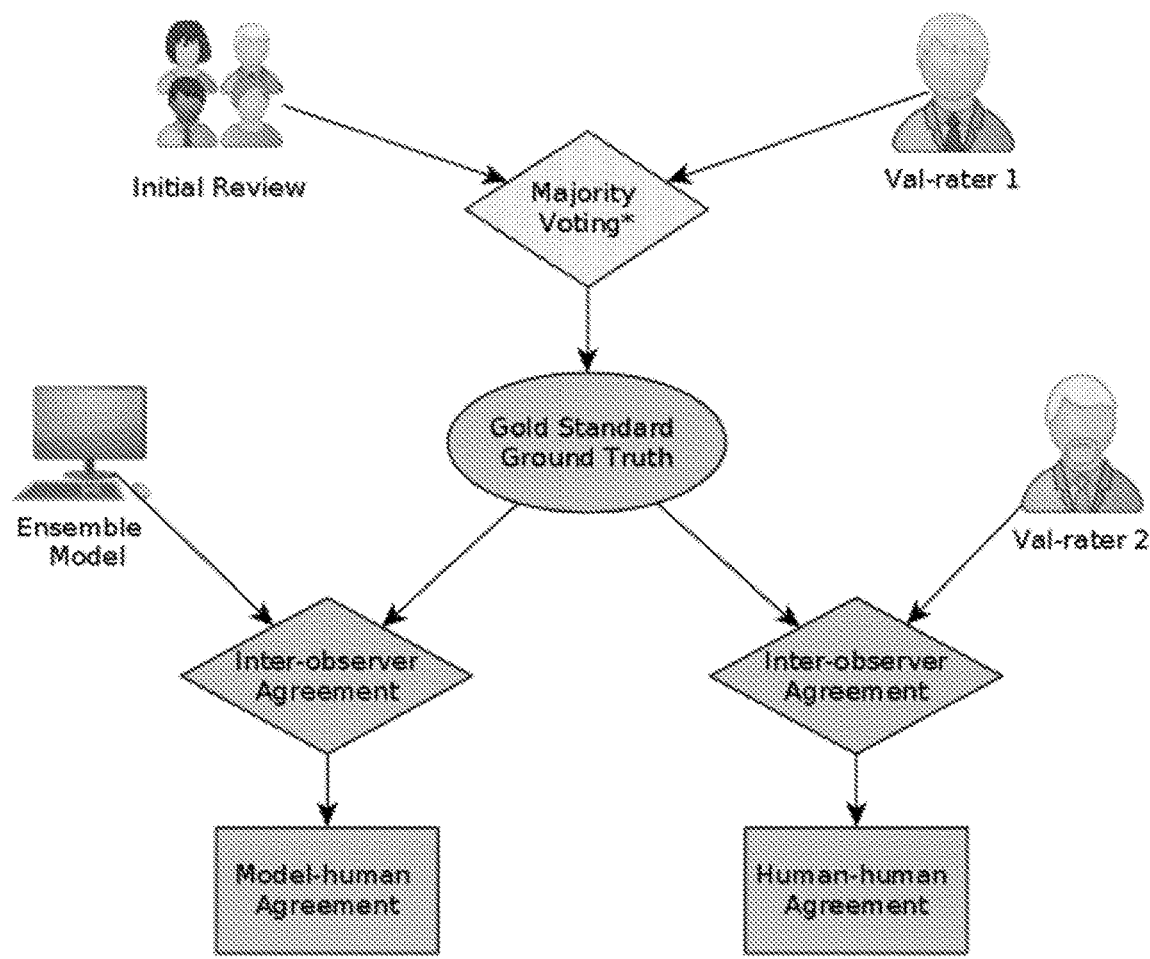
FIG. 9 shows an example of a process for evaluating whether a model trained in accordance with some embodiments of the disclosed subject matter is identifying histological features that a human expert is likely to use in making a diagnosis.

FIG. 9 shows an example 900 of a procedure that can be used to select diagnostic images from a dataset and evaluate whether a model trained in accordance with some embodiments of the disclosed subject matter is identifying histological features that a human expert is likely to use in making a diagnosis.

In some embodiments, a set of images can be generated using any suitable technique or combination of techniques. For example, images can be captured in vivo and/or ex vivo during brain surgery with a CLE device. As another example, images can be retrieved that were generated during previous surgeries. In one particular example, intraoperative CLE images were acquired both in vivo and ex vivo by 4 neurosurgeons from seventy-four adult patients (31 male and 43 female) with a mean age of 47.5 years. For in vivo imaging, multiple locations of the tissue around a lesion were imaged and excised from the patient. For ex vivo imaging, tissue samples suspicious for tumor were excised, placed on gauze and imaged on a separate work station in the operating room. Multiple images were obtained from each biopsy location. From these 74 brain tumor patients, a dataset of 20,734 CLE images were generated. Co-registration of the CLE probe with the image guided surgical system allowed precise intraoperative mapping of CLE images with regard to the site of the biopsy. The only fluorophore administered was FNa (5 mL, 10%) that was injected intravenously during the surgery. Precise location of the areas imaged with the CLE was marked with tissue ink, and imaged tissue was sent to the pathology laboratory for formalin fixation, paraffin embedding and histological sections preparation. Final histopathological assessment was performed by standard light microscopic evaluation of 10-μm-thick hematoxylin and eosin ("H & E")-stained sections.

In some embodiment, the diagnostic quality of each CLE image can be determined by experts (e.g., neuropathologists, neurosurgeons, etc.) in an initial review. For example, the experts can review each of the images in the set of images to determine whether histopathological features are clearly identifiable. Additionally, in some embodiments, the image can be compared to images of tissue samples from the same location that were captured using standard light microscopic imaging of 10-micrometed (μm)-thick hematoxylin and eosin ("H & E")-stained sections. When a CLE image reveals clearly identifiable histopathological feature, it can be labeled as diagnostic; and if it does not it can labeled as non-diagnostic. In some embodiments, two or more experts can review the images and H & E-stained sections collectively, and make a collective judgment of which images are diagnostic or non-diagnostic. Additionally or alternatively, one or more experts can review the images H & E-stained sections independently, and a final label can be determined based on the consensus of determinations from various experts and/or groups of experts. In some embodiments, the initial review can be used to generate the classifications received by process 300 and/or process 800 at 304 and 804, respectively. In one particular example, each CLE image of the 20,734 CLE images was reviewed for diagnostic quality by a neuropathologist and two neurosurgeons who were not involved in the surgeries in an initial review. After the initial review, the dataset was divided into two main subsets on patient level (i.e., patients were assigned to a subset, and all images associated with that patient were placed in that subset), a development set and a test set. The total number of patients and images used at each stage are shown below in Table 5. Each subset contained images from various tumor types (mainly from gliomas and meningiomas). Images from the test set were not used in training any of the CNNs.

TABLE 5

|  | Development | Test |
| --- | --- | --- |
| Number of Patients (total) | 59 | 15 |
| Gliomas | 16 | 5 |
| Meningiomas | 24 | 6 |
| Other neoplasms | 19 | 4 |

TABLE 5-continued

|  | Development | Test |
| --- | --- | --- |
| Number of Images (total) | 16,366 | 4,171 |
| Diagnostic | 8,023 | 2,071 |
| Nondiagnostic | 8,343 | 2,100 |

In some embodiments, the labels generated using the initial review can be used to train one or more CNNs (e.g., as described above in connection with 808 of FIG. 8) using a training set and validation set (which can, for example, be further divided into subsets that are used to train various different CNNs) selected from the set of images, and tested using the remaining images (i.e., the test set).

In some embodiments, one or more additional experts can review a subset of the test images without having access to the H & E-stained sections, and can classify each as being diagnostic or non-diagnostic. When the additional expert(s) makes the same classification that was made during the initial review, that image can be included within a "gold standard" set of images for which an expert human reviewer that did not have the benefit of the H & E-stained sections came to the same conclusion as the initial reviewers that did. In one particular example, the test set included 4,171 CLE images randomly chosen from various patients, and the validation set reviewed by an additional human expert ("val-rater 1") included 540 images randomly chosen from the test set. Note that, in some embodiments, multiple "gold standard" image sets can be defined based on the agreement between the initial review and a review by a second human expert (e.g., "val-rater 2") that does not have the benefit of the H & E-stained sections (e.g., to provide a "gold-standard" for comparing the performance of the val-rater 1). In one particular example, the positions of val-rater 1 and val-rater 2 in FIG. 9 can be reversed to generate a second set of gold standard images.

In some embodiments, trained CNNs (individually and/or as part of an ensemble), can classify images from the test dataset to determine the accuracy of the trained CNN(s). In one particular example, the classification of the trained CNN(s) can be compared to the classification by the additional expert human reviewer(s). Table 6 shows the rate at which a trained CNN ensemble (i.e., an ensemble of GoogLeNet-based CNNs trained using deep fine tuning, as described below in connection with FIG. 10) and two additional expert human reviewers correctly classified images from the validation set (i.e., the rate at which they agreed with the initial review), and the rate at which they agreed on the "gold standard" images.

TABLE 6

| Dataset | Whole Val Review | | Gold-Standard |
| --- | --- | --- | --- |
| Rater | General Agreement | Cohen's Kappa | General Agreement |
| Val-Rater 1 | 66% | 0.32, Fair | 67% |
| Val-Rater 2 | 73% | 0.47, Moderate | 75% |
| Model | 76% | 0.47, Moderate | 85% |

In Table 6, the values under "Whole Val Review" illustrate agreement between the rater (e.g., Val-Rater 1, Val-Rater 2, or Model), and the initial review. While values under "Gold-Standard" represent agreement between the rater and a set of "gold standard" images that was generated based on review of one or more human experts other than that rater. For example, Val-Rater 2 was in agreement with the labels of Val-Rater 1 and the initial review for 75% of images in a set of images on which Val-Rater 1 and the initial review were in agreement (which can be referred to as, e.g., gold standard set 1). As another example, Val-Rater 1 was in agreement with the labels of Val-Rater 2 and the initial review for 67% of images in a set of images on which Val-Rater 2 and the initial review were in agreement (which can be referred to as, e.g., gold standard set 2). As yet another example, the model was in agreement with the labels for 85% of the images of gold standard set 1 and gold standard set 2. As shown in Table 6, the model agreed with the initial review more often than each val-rater's agreement with the initial review, which suggests that the model successfully learned the histological features of the CLE images that are more probable to be noticed by the neurosurgeons when the corresponding H & E-stained histological slides were also provided for reference.

Figure 10:
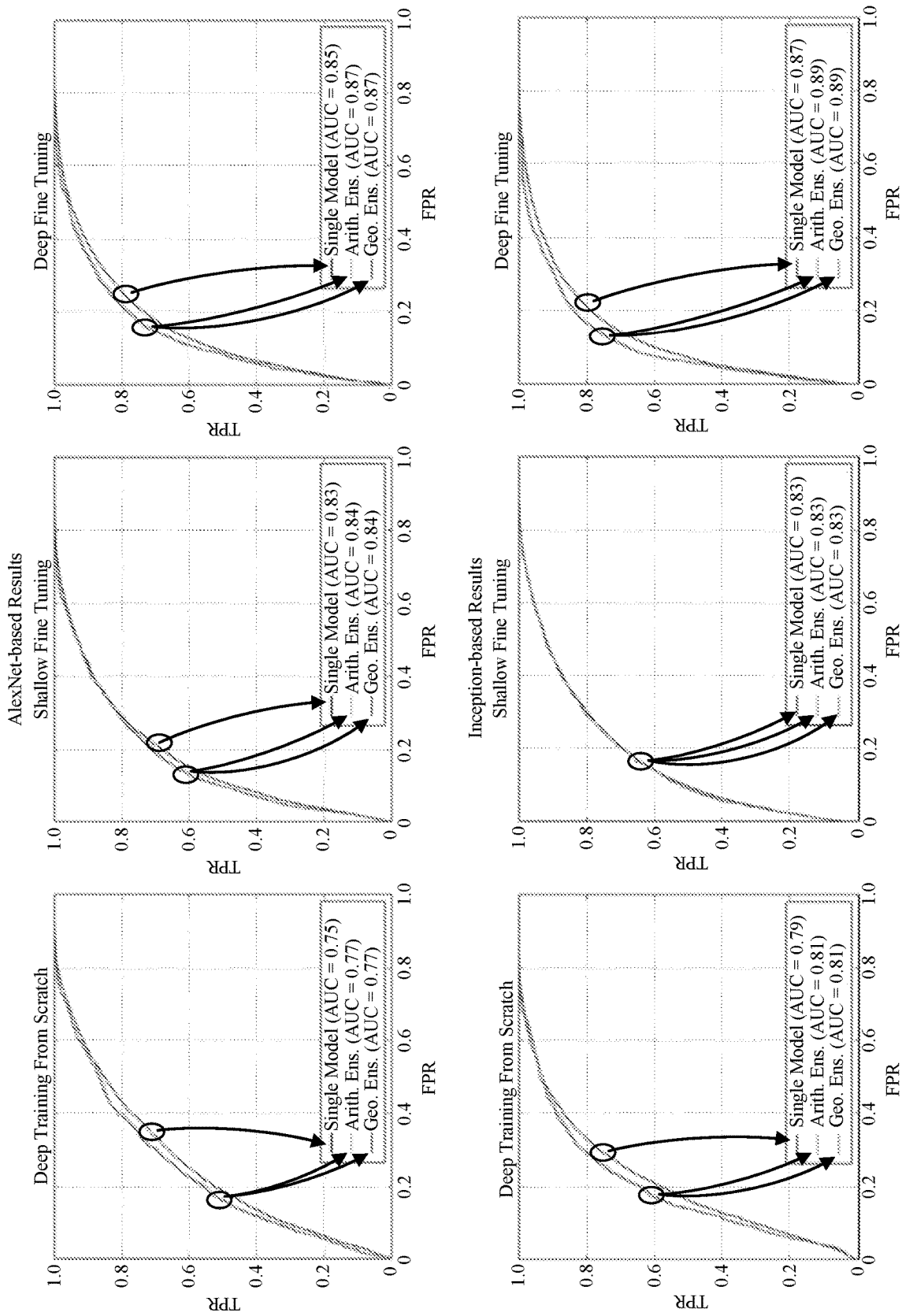
FIG. 10 shows examples of plots comparing the performance of a particular training modality across different model configurations in accordance with some embodiments of the disclosed subject matter.

FIG. 10 shows examples of plots comparing the performance of a particular training modality across different model configurations in accordance with some embodiments of the disclosed subject matter. The results of FIG. 10 represent two CNN architectures that were trained sing various training modalities. As described in Krizhevsky et al., an AlexNet-based CNN had five convolutional layers. The first two convolutional layers had 96 and 256 filters of size 11×11 and 5×5 with max pooling. The third, fourth, and fifth convolutional layers were connected back to back without any pooling in between. The third convolutional layer had 384 filters of size 3×3×256, the fourth layer had 384 filters of size 3×3×192 and the fifth layer had 256 filters of size 3×3×192 with max pooling.

As described in Szegedy et al., a GoogLeNet-based CNN had 22 layers with parameters and 9 inception modules. As described above in connection with FIG. 4, each inception module was a combination of filters of size 1×1, 3×3, 5×5 and a 3×3 max pooling in parallel, and the output filter banks concatenated into an input single vector for the next stage.

After the initial data split, a patient-based k-fold cross validation was performed for model development. The 59 cases in Table 5 that were allocated for model development were divided into five groups. Since CNNs typically require a large set of hyperparameters to be defined optimally (i.e., initial value of the learning rate and its lowering policy, momentum, batch size, etc.), different values were used with grid searching throughout the model development process. For every set of feasible parameters, each model was trained on four folds, and validated on the fifth left-out group of patients (i.e., four folds were included in the training set, and the remaining fold was included in the validation set). The set of hyperparameters which produced the minimum average loss was employed for each set of experiments for which results are shown in FIG. 10.

In total, 42 models were developed (30 single models, and 12 ensemble models) using the two network architectures and three training regimes (i.e., deep training from scratch, shallow fine-tuning and deep fine-tuning). Note that the pre-trained model used for the AlexNet-based CNNs was a snapshot of iteration 360,000 of training the model on images from the ImageNet dataset with 1,000 classes, and the pre-trained model used for the GoogLeNet-based CNNs was a snapshot of iteration 2,400,000 of training the model on images from the ImageNet dataset with 1,000 classes.

The results shown in FIG. 10 correspond to three different training regimes, including deep training or training from scratch ("DT"), shallow fine-tuning ("SFT"), and deep fine-tuning ("DFT"). In DT, model weights for the entire model were initialized randomly and modified with nonzero learning rates (i.e., only the architecture, but none of the weights from the pre-trained models were used). In SFT, model weights were initialized with the corresponding values from the pre-trained model and the values were fixed for the period of training (i.e., not trained), but the last fully connected layer was initialized randomly and tuned during training. In DFT, model weights were initialized to the corresponding values from the pre-trained model and tuned during training, and the last fully connected layer was initialized randomly and tuned during training.

The SFT and DFT experiments required a 10 times smaller initial learning rates (i.e., 0.001) compared to the DT regime initial learning rate (i.e., 0.01). To avoid overfitting, the training process was stopped after 3 epochs of consistent loss increment on the validation dataset, and a dropout layer (with ratio=0.5) and L2 regularization (with $\lambda$=0.005) were also used.

Accuracy rates of the 42 models on the 4,171 test images (where a correct classification is based on agreement with the initial review) are below in Table 7. As shown in Table 7 and in FIG. 10, GoogLeNet-based CNNs generally produced more precise predictions about the diagnostic quality of images compared with the AlexNet-based CNNs when the DT and DFT training regimes were used in training, while the SFT training regime resulted in slightly better accuracy of the AlexNet-based CNNs in some situations.

FIG. 10 shows results of an ROC analysis for each of the two networks and three training regimes to see how the ensemble of models performed compared to the best performing single models. The AUC value increased by 2% for both networks with DT and DFT when the ensemble is used instead of the single model. This effect is not as evident with the AlexNet-based CNNs trained using SFT, and is negligible with the GoogLeNet-based CNNs trained using SFT. The two arithmetic and geometric ensemble models produced roughly similar results (paired t-test: P value<0.05). Note that the SFT trained models displayed less sensitivity to the ensemble effect compared to DT and DFT, which is likely due to the fact that they represent identical models except in the softmax classifier layer, which was initialized to random values and adjusted through training.

TABLE 7

| Training Regime | AlexNet-based | | | GoogLeNet-based | | |
|---|---|---|---|---|---|---|
| | DT | SFT | DFT | DT | SFT | DFT |
| Model 1 | 0.685 | 0.760 | 0.760 | 0.731 | 0.746 | 0.746 |
| Model 2 | 0.658 | 0.749 | 0.755 | 0.750 | 0.746 | 0.805 |
| Model 3 | 0.677 | 0.751 | 0.765 | 0.715 | 0.747 | 0.797 |
| Model 4 | 0.681 | 0.754 | 0.771 | 0.739 | 0.743 | 0.811 |
| Model 5 | 0.699 | 0.753 | 0.775 | 0.721 | 0.747 | 0.777 |
| Mean | 0.680 | 0.753 | 0.765 | 0.731 | 0.746 | 0.787 |
| Arthimatic Ensemble | 0.704 | 0.755 | 0.788 | 0.754 | 0.750 | 0.816 |
| Geometetric Ensemble | 0.703 | 0.758 | 0.786 | 0.755 | 0.751 | 0.818 |

Figure 11:
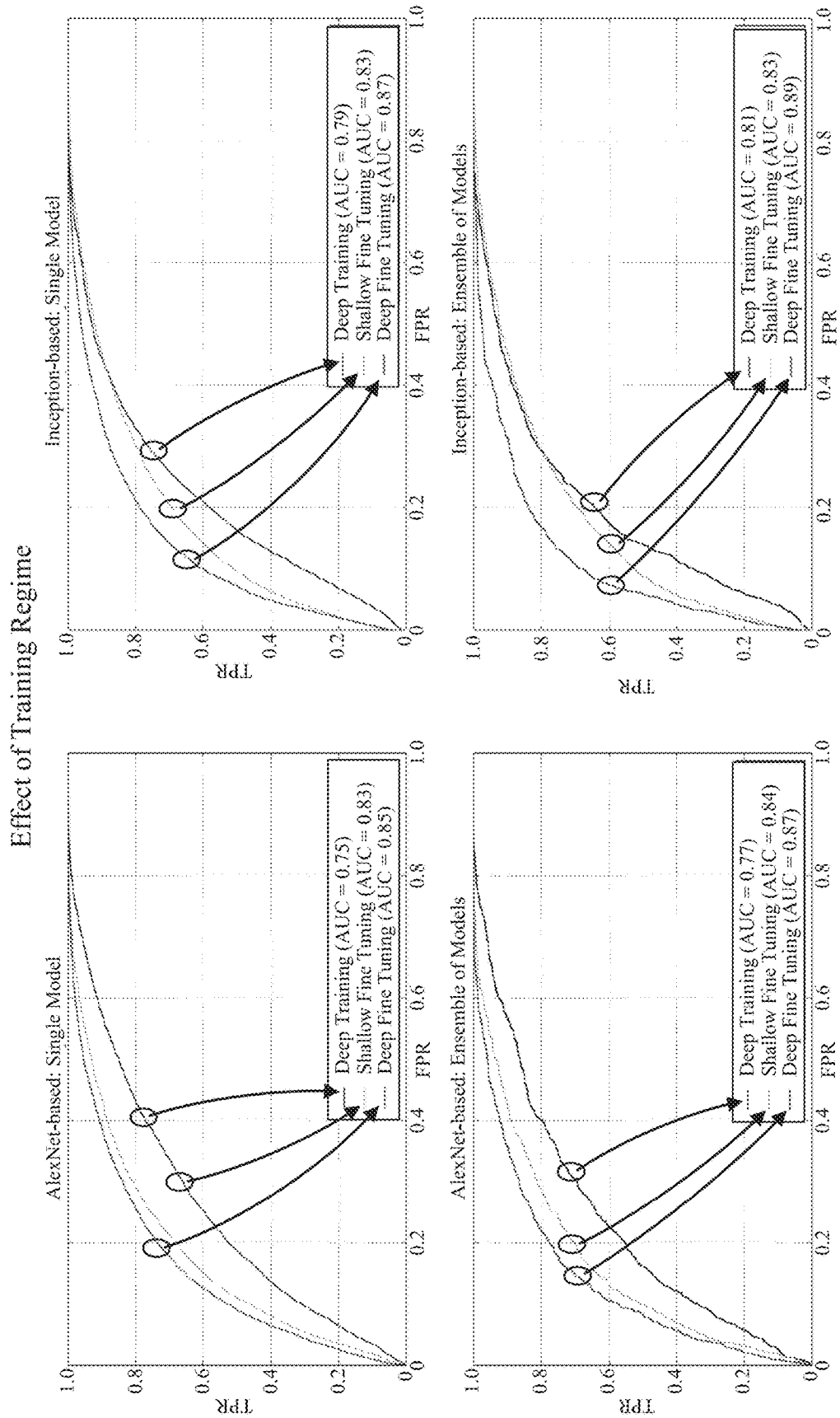
FIG. 11 shows examples of plots comparing the performance of a particular model configuration across different training modalities in accordance with some embodiments of the disclosed subject matter.

FIG. 11 shows examples of plots comparing the performance of a particular model configuration across different training modalities in accordance with some embodiments of the disclosed subject matter. In particular, FIG. 11 shows the results of an ROC analysis when comparing the three training regimes in each network architecture and single/ensemble states. In all paired comparisons, DFT outperformed SFT, and SFT outperformed DT (paired t-test: P value<0.05). Additionally, comparisons of the AUC elevation from DT to DFT regimes illustrate see how much of the performance improvement can be attributed to moving from DT to SFT, and moving from SFT to DFT. For the AlexNet-based CNNs, 70-80% of the improvement occurred in the DT to SFT transformation (with differences depending on whether it's a single model or ensemble model being evaluated), while for the GoogLeNet-based CNNs, the AUC improvement caused by transforming the training regime from DT to SFT (2%) is only 25% of the total improvement from DT to DFT for the ensemble model, but is roughly evenly divided between the two transformations for the single model.

As can be appreciated from FIGS. 10 and 11, AlexNet-based CNNs mainly benefited from fine-tuning the classification layer, whereas fine-tuning other layers (feature extractors) had a smaller contribution. However, for GoogLeNet-based CNNs, fine-tuning the feature extractors provided more benefit than modifying the classifier layer alone.

Figure 12:
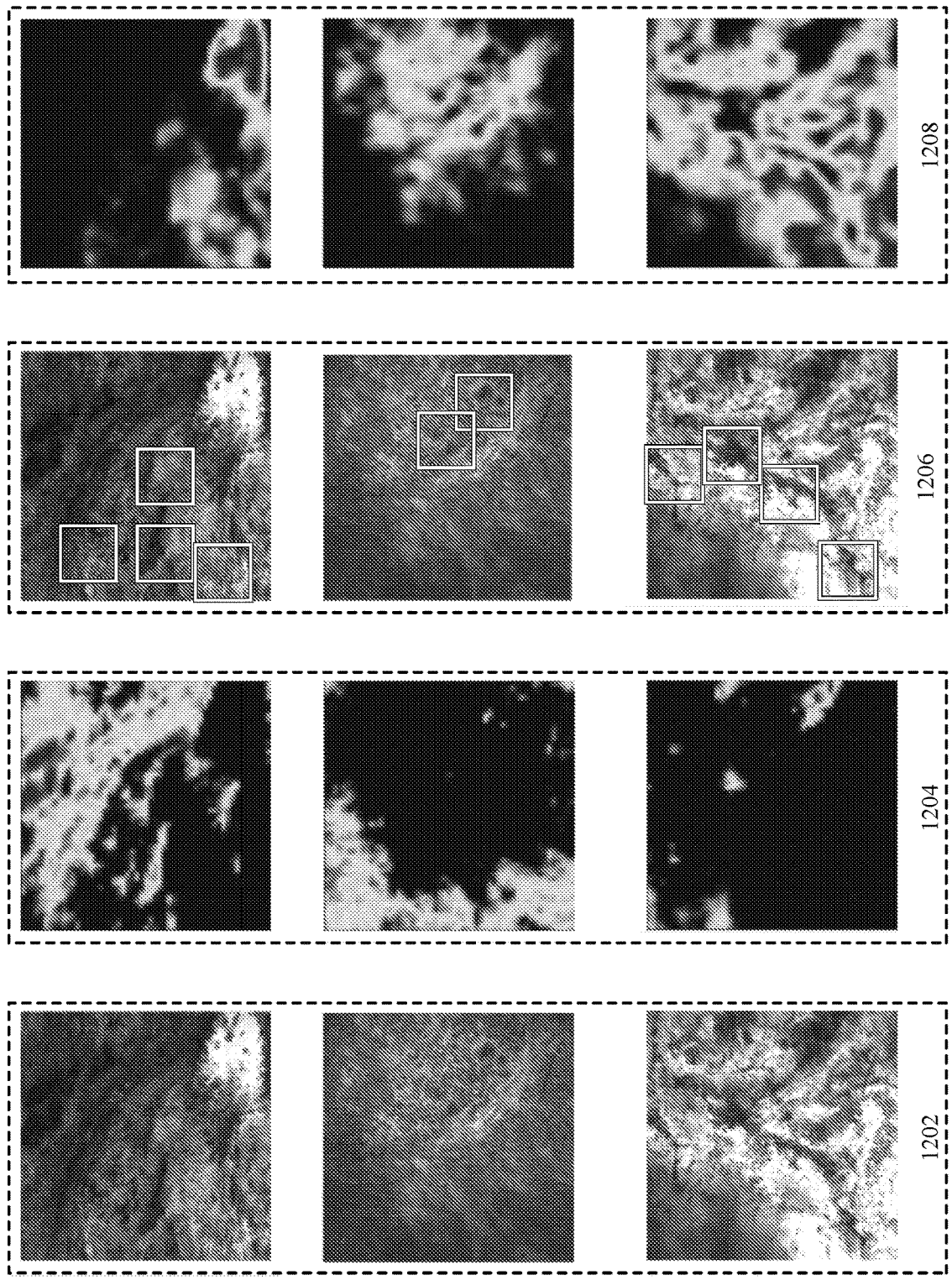
FIG. 12 shows examples of CLE images, outputs from layers of a trained CNN, and portions of the CLE images that have been identified using unsupervised feature localization techniques implemented in accordance with some embodiments of the disclosed subject matter.

FIG. 12 shows examples of CLE images, outputs from layers of a trained CNN, and portions of the CLE images that have been identified using unsupervised feature localization techniques implemented in accordance with some embodiments of the disclosed subject matter.

In some embodiments, histological features that may potentially be of use in making a diagnosis can be located using outputs from one or more layers of a trained CNN(s). For example, activation of neurons in the first convolutional layer of an AlexNet-based CNN can be visualized. Neurons that present high activation to the location of cellular structures in the input image can be selected, and may be consistent with diverse diagnostic images.

As another example, a sliding window of size 227×227 pixels (which is the size of an AlexNet-based CNN input after input cropping) with stride of 79 pixels over the diagnostic CLE images (1024×1024 pixels) can be used to generate a 10×10 matrix that provides the diagnostic value of different locations of the input image (e.g., as a diagnostic map). The locations of input images corresponding to the highest activations of the diagnostic map can be detected and marked with a bounding box.

Input CLE images are shown in box 1202 of FIG. 12. The visualizations in box 1204 correspond to the CLE images in box 1202, and were generated from outputs of the first layer of an AlexNet-based CNN (specifically conv1, neuron 24). The visualizations of box 1204 highlight of the cellular areas present in the images.

The windows in the images of box 1206 represent windows in the image which has relatively high activations of the diagnostic map, and may correspond to diagnostic aggregates of abnormally large malignant glioma cells and atypically hypercellular areas.

The visualizations in box 1206 correspond to the CLE images in box 1204 and were generated from outputs of the first layer of an AlexNet-based CNN (specifically conv1, neuron 22). The highlighted areas correspond to areas with increased fluorescein signal, a sign specific to brain tumor regions due to their representation of areas with blood brain barrier disruption which correspond to the tumor areas visible on a contrast enhanced MR imaging.

In general, the sliding window technique described above, and selected colored activation maps generally were not influenced by red blood cell contamination, as they mostly highlighted tumor and brain cells rather than hypercellular areas due to bleeding.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

What is claimed is:

1. A method for selectively presenting images captured by a confocal laser endomicroscopy (CLE) device, comprising:
   receiving a first image captured by a CLE device during brain surgery;
   providing the first image to a convolution neural network trained using at least a plurality of images, wherein each of the plurality of images is an image of brain tissue that was captured using CLE techniques and is labeled as either a diagnostic image or a non-diagnostic image, wherein images labeled as diagnostic provide at least a threshold level of identifiable histological features and images labeled as non-diagnostic do not provide the threshold level of identifiable histological features;
   receiving an indication, based on a first output of the convolution neural network, of a first likelihood that the first image is a diagnostic image;
   determining, based on the first likelihood, that the first image is a diagnostic image; and
   in response to determining that the first image is a diagnostic image, causing the first image to be presented during the brain surgery.

2. The method of claim 1, further comprising:
   receiving a second image captured by the CLE device during the brain surgery;
   providing the second image to the convolution neural network;
   receiving an indication, based on a second output of the convolution neural network, of a second likelihood that the second image is a diagnostic image;
   determining, based on the second likelihood, that the second image is not a diagnostic image;
   in response to determining that the second image is not a diagnostic image, inhibiting the second image from being presented during the brain surgery.

3. The method of claim 1, wherein determining that the first image is a diagnostic image comprises determining that the first likelihood is at least a threshold probability.

4. The method of claim 3, wherein the threshold probability is about 0.5.

5. The method of claim 1, further comprising:
   receiving a plurality of additional images captured by the CLE device during the brain surgery at a rate of between about 0.8 and about 1.2 frames per second;
   classifying each of the plurality of additional images in real time during the brain surgery using the convolution neural network;
   indicating, based on the classifications output by the convolutional neural network, that a first subset of the plurality of additional images are diagnostic images; and
   indicating, based on the classification output by the convolutional neural network, that a second subset of the plurality of plurality of additional images are non-diagnostic image.

6. The method of claim 1, further comprising:
   receiving, by a server, the first image from a computing device that communicates with the CLE device over a local connection, and that is remote from the server; and
   sending, to the remote computing device, an indication that the first image is a diagnostic image.

7. The method of claim 6, further comprising storing, by the server, the first image in memory associated with the server in connection with an indication that the first image is a diagnostic image.

8. The method of claim 1, wherein an architecture of the convolutional neural network is based on an AlexNet convolutional neural network.

9. The method of claim 1, wherein an architecture of the convolutional neural network is based on a GoogLeNet convolutional neural network.

10. A system, comprising:
    a confocal laser endomicroscopy (CLE) device, comprising:
       a rigid probe; and
       a light source, wherein the confocal laser endomicroscopy device is configured to generate image data representing brain tissue during brain surgery; and
    a computing device comprising:
       a hardware processor; and
       memory storing computer-executable instructions that, when executed by the processor, cause the processor to:
          receive, from the CLE device, a first image captured during a brain surgery;
          provide the first image to a convolution neural network trained using at least a plurality of images, wherein each of the plurality of images is an image of brain tissue that was captured using CLE techniques, and is labeled as either a diagnostic image or a non-diagnostic image, wherein images labeled as diagnostic provide at least a threshold level of identifiable histological features and images labeled as non-diagnostic do not provide the threshold level of identifiable histological features;
          receive an indication, based on a first output of the convolution neural network, of a first likelihood that the first image is a diagnostic image;
          determine, based on the first likelihood, that the first image is a diagnostic image; and
          in response to determining that the first image is a diagnostic image, present the first image during the brain surgery.

11. The system of claim 10, wherein the computer-executable instructions, when executed by the processor, further cause the processor to:
    receive a second image captured by the CLE device during the brain surgery;
    provide the second image to the convolution neural network;
    receive an indication, based on a second output of the convolution neural network, of a second likelihood that the second image is a diagnostic image;
    determine, based on the second likelihood, that the second image is not a diagnostic image;
    in response to determining that the second image is not a diagnostic image, inhibit the second image from being presented during the brain surgery.

12. The system of claim 10, wherein the computer-executable instructions, when executed by the processor, further cause the processor to:
receive, from the CLE device, a plurality of additional images captured by the CLE device during the brain surgery at a rate of between about 0.8 and about 1.2 frames per second;
classify each of the plurality of additional images in real time during the brain surgery using the convolution neural network;
indicate, based on the classifications output by the convolutional neural network, that a first subset of the plurality of additional images are diagnostic images; and
indicating, based on the classification output by the convolutional neural network, that a second subset of the plurality of plurality of additional images are non-diagnostic image.

13. The system of claim 10, wherein the convolutional neural network is executed by the computing device.

14. The system of claim 10, wherein the convolutional neural network is executed by a remote server.

15. A method for selectively presenting images captured by a confocal laser endomicroscopy (CLE) device, comprising:
receiving an image captured by a CLE device during brain surgery;
providing the first image to a plurality of convolution neural networks trained using at least a subset of images from a plurality of images,
wherein the plurality of images are images of brain tissue captured using CLE techniques and labeled as either a diagnostic image or a non-diagnostic image, wherein images labeled as diagnostic provide at least a threshold level of identifiable histological features and images labeled as non-diagnostic do not provide the threshold level of identifiable histological features, and
wherein each of the plurality of convolutional neural networks was trained with a validation subset from the plurality of images that is different than the validation subset used to train each of the other convolution neural networks in the plurality of convolutional neural networks;
receiving an indication, based on first outputs of the plurality of convolution neural networks, of a first likelihood that the first image is a diagnostic image;
determining, based on the first likelihood, that the first image is a diagnostic image; and
in response to determining that the first image is a diagnostic image, causing the first image to be presented during the brain surgery.

16. The method of claim 15, wherein the indication of the first likelihood is calculated based on a combination of the outputs of each of the plurality of convolutional neural networks.

17. The method of claim 16, wherein the first likelihood is the arithmetic mean of the outputs of each of the plurality of convolutional neural networks.

18. The method of claim 16, wherein the first likelihood is the geometric mean of the outputs of each of the plurality of convolutional neural networks.

19. The method of claim 15, further comprising:
receiving, for each of the plurality of images, an indication of whether the image is diagnostic or non-diagnostic;
dividing the plurality of images into a development subset and a testing subset;
dividing the development subset into l folds, wherein l is the number of convolutional neural networks in the plurality of convolutional neural networks; and
training each of the l convolutional neural networks using l–1 of the folds as a training set and using one of the folds as a validation set, wherein each of the l convolutional neural networks is trained using a different fold as the validation set.

20. The method of claim 19, wherein a plurality of layers of each of the plurality of convolutional neural networks is trained using weights that are initialized to values set based on weights in a pre-trained convolutional neural network with the same architecture, wherein the pre-trained convolutional neural network was trained to recognize a multitude of classes of common objects.

21. The method of claim 20, wherein the multitude of classes of common objects correspond to at least a portion of the classes defined by the ImageNet dataset of labeled images.

* * * * *